(12) United States Patent
Brown et al.

(10) Patent No.: US 10,945,935 B2
(45) Date of Patent: Mar. 16, 2021

(54) SHAMPOO COMPOSITION CONTAINING A GEL NETWORK

(71) Applicant: The Procter & Gamble Company, Cincinnati, OH (US)

(72) Inventors: Mark Anthony Brown, Union, KY (US); Michelle Ramos, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 104 days.

(21) Appl. No.: 15/635,633

(22) Filed: Jun. 28, 2017

(65) Prior Publication Data

US 2017/0367955 A1    Dec. 28, 2017

Related U.S. Application Data

(63) Continuation of application No. PCT/US2017/039444, filed on Jun. 27, 2017.

(60) Provisional application No. 62/354,886, filed on Jun. 27, 2016, provisional application No. 62/404,486, filed on Oct. 5, 2016.

(51) Int. Cl.
| | |
|---|---|
| *A61K 8/00* | (2006.01) |
| *A61K 8/46* | (2006.01) |
| *A61Q 5/02* | (2006.01) |
| *A61K 8/04* | (2006.01) |
| *A61K 8/34* | (2006.01) |
| *A61K 8/41* | (2006.01) |
| *A61K 8/44* | (2006.01) |
| *A61K 8/73* | (2006.01) |

(52) U.S. Cl.
CPC .............. *A61K 8/463* (2013.01); *A61K 8/042* (2013.01); *A61K 8/342* (2013.01); *A61K 8/41* (2013.01); *A61K 8/416* (2013.01); *A61K 8/442* (2013.01); *A61K 8/466* (2013.01); *A61K 8/737* (2013.01); *A61Q 5/02* (2013.01); *A61K 2800/34* (2013.01); *A61K 2800/5426* (2013.01); *A61K 2800/594* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 2,326,733 A | 8/1943 | Fisher | |
| 2,396,278 A | 3/1946 | Otto | |
| 2,430,890 A | 3/1948 | Lynch | |
| 2,486,921 A | 11/1949 | Byerly | |
| 2,486,922 A | 11/1949 | Bruce | |
| 2,528,378 A | 10/1950 | McCabe, Jr. | |
| 2,658,072 A | 11/1953 | Kosmin | |
| 2,694,668 A | 11/1954 | Fricke | |
| 2,786,847 A | 3/1957 | Cislak | |
| 2,798,053 A | 7/1957 | Brown | |
| 2,809,971 A | 10/1957 | Jack | |
| 2,826,551 A | 3/1958 | Geen | |
| 3,152,046 A | 10/1964 | Maria | |
| 3,155,591 A | 11/1964 | Harry | |
| 3,236,733 A | 2/1966 | Karsten | |
| 3,332,880 A | 7/1967 | Adriaan | |
| 3,589,999 A | 6/1971 | Mcrae | |
| 3,590,035 A | 6/1971 | Damico | |
| 3,753,196 A | 8/1973 | Kurtz | |
| 3,761,418 A | 9/1973 | Parran | |
| 3,773,770 A | 11/1973 | Damico | |
| 3,852,441 A | 12/1974 | Kooistra | |
| 3,929,678 A | 12/1975 | Laughlin et al. | |
| 3,940,482 A | 2/1976 | Grand | |
| 3,958,581 A | 5/1976 | Abegg | |
| 3,959,461 A | 5/1976 | Bailey | |
| 3,964,500 A | 6/1976 | Drakoff | |
| 4,055,655 A | 10/1977 | Maurer | |
| 4,089,945 A | 5/1978 | Brinkman | |
| 4,152,416 A | 5/1979 | Marra | |
| 4,161,426 A | 7/1979 | Kneer | |
| 4,197,865 A | 4/1980 | Jacquet | |
| 4,217,914 A | 8/1980 | Jacquet | |

(Continued)

FOREIGN PATENT DOCUMENTS

| | | |
|---|---|---|
| AU | 2012337567 B2 | 4/2017 |
| CA | 2143558 A1 | 8/1996 |

(Continued)

OTHER PUBLICATIONS

"Herbal Essence Shampoo", Mintel, Jun. 1, 2014.

(Continued)

*Primary Examiner* — Necholus Ogden, Jr.
(74) *Attorney, Agent, or Firm* — Angela K. Haughey

(57) ABSTRACT

A shampoo composition and a method of making a shampoo composition which delivers both good conditioning benefits and good lather performance. The shampoo composition comprises a dispersed gel network phase comprising: from about 2.8 weight % to about 8 wt % of one or more fatty alcohols; at least 0.01% of one or more secondary surfactants, wherein the secondary surfactant comprises sodium laureth-n sulfate wherein n is from about 0 to about 5; and water; and from about 5% to about 50% of a detersive surfactant; from about 0.02% to about 1.50% of a material selected from the group consisting of structurants, suspending agents and mixtures thereof, from about 0.5 to about 1% of a cationic deposition polymer; and at least 20% of an aqueous carrier.

12 Claims, 2 Drawing Sheets

(56) References Cited

U.S. PATENT DOCUMENTS

| | | |
|---|---|---|
| 4,323,683 A | 4/1982 | Bolich, Jr. |
| 4,345,080 A | 8/1982 | Bolich, Jr. |
| 4,364,387 A | 12/1982 | Larkin |
| 4,379,753 A | 4/1983 | Bolich, Jr. |
| 4,381,919 A | 5/1983 | Jacquet |
| 4,387,090 A | 6/1983 | Bolich, Jr. |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De |
| 4,565,647 A | 1/1986 | Llenado |
| 4,604,272 A | 8/1986 | Kratel |
| 4,608,183 A | 8/1986 | Rossmoore |
| 4,663,158 A | 5/1987 | Wolfram |
| 4,666,616 A | 5/1987 | Rossmoore |
| 4,670,430 A | 6/1987 | Imamura |
| 4,686,254 A | 8/1987 | Lochhead |
| 4,704,272 A | 11/1987 | Oh |
| 4,708,863 A | 11/1987 | Bews |
| 4,726,915 A | 2/1988 | Verdicchio |
| 4,788,006 A | 11/1988 | Bolich, Jr. |
| 4,834,767 A | 5/1989 | Helioff |
| 4,885,107 A | 12/1989 | Wetzel |
| 4,898,585 A | 2/1990 | Borsanyi |
| 5,034,218 A | 7/1991 | Duvel |
| 5,057,153 A | 10/1991 | Ruggiero |
| 5,104,646 A | 4/1992 | Bolich, Jr. |
| 5,106,609 A | 4/1992 | Bolich, Jr. |
| 5,106,613 A | 4/1992 | Hartnett |
| 5,114,898 A | 5/1992 | Pinnavaia |
| 5,154,847 A | 10/1992 | Lapetina |
| 5,186,928 A | 2/1993 | Birtwistle |
| 5,202,048 A | 4/1993 | Bartolo |
| 5,227,156 A | 7/1993 | Wiese |
| 5,248,445 A | 9/1993 | Rizvi |
| RE34,584 E | 4/1994 | Grote |
| 5,358,667 A | 10/1994 | Bergmann |
| 5,360,581 A | 11/1994 | Rizvi |
| 5,462,589 A | 10/1995 | Nicholas |
| 5,466,425 A | 11/1995 | Adams |
| 5,478,501 A | 12/1995 | Rau |
| 5,495,538 A | 2/1996 | Fan |
| 5,518,774 A | 5/1996 | Kappock |
| 5,540,954 A | 7/1996 | Nicholas |
| 5,562,995 A | 10/1996 | Kappock |
| 5,609,862 A | 3/1997 | Chen et al. |
| 5,614,538 A | 3/1997 | Nelson, Jr. |
| 5,674,478 A | 10/1997 | Dodd et al. |
| 5,696,169 A | 12/1997 | Otsu |
| 5,710,114 A | 1/1998 | Pyles |
| 5,726,137 A | 3/1998 | Patel |
| 5,750,122 A | 5/1998 | Evans |
| 5,756,076 A | 5/1998 | Cervantes |
| 5,776,444 A | 7/1998 | Birtwistle et al. |
| 5,785,962 A | 7/1998 | Hinz |
| 5,798,121 A | 8/1998 | Cauwet |
| 5,811,487 A | 9/1998 | Schulz, Jr. et al. |
| 5,837,661 A | 11/1998 | Evans |
| 5,853,707 A | 12/1998 | Wells |
| 5,854,319 A | 12/1998 | Olenick, Jr. |
| 5,874,476 A | 2/1999 | Hsu |
| 5,876,705 A | 3/1999 | Uchiyama |
| 5,880,076 A | 3/1999 | Vermeer |
| 5,883,154 A | 3/1999 | Kappock |
| 5,939,059 A | 8/1999 | Franklin |
| 5,939,203 A | 8/1999 | Kappock |
| 5,955,066 A | 9/1999 | Sako |
| 5,965,515 A | 10/1999 | Rau |
| 5,977,036 A | 11/1999 | Guskey |
| 5,997,036 A | 12/1999 | Hamada |
| 5,997,851 A | 12/1999 | Cox |
| 6,017,562 A | 1/2000 | Kaufman |
| 6,034,043 A | 3/2000 | Fujiwara |
| 6,183,766 B1 | 2/2001 | Sine |
| 6,303,109 B1 | 10/2001 | Foerster |
| 6,309,628 B1 | 10/2001 | Ansmann |
| 6,333,040 B1 | 12/2001 | Boyxen |
| RE37,793 E | 7/2002 | Domenico |
| 6,432,420 B2 | 8/2002 | Ellis |
| 6,451,300 B1 | 9/2002 | Dunlop et al. |
| 6,521,238 B1 | 2/2003 | Muller |
| 6,521,239 B1 | 2/2003 | Breton |
| RE38,130 E | 6/2003 | Adams |
| 6,719,967 B1 | 4/2004 | Brown |
| 6,774,096 B1 | 8/2004 | Paye |
| 6,908,912 B2 | 6/2005 | Rioux |
| 6,991,799 B2 | 1/2006 | Pham et al. |
| 7,303,744 B2 | 12/2007 | Wells |
| 7,531,497 B2 | 5/2009 | Midha et al. |
| 7,560,125 B2 | 7/2009 | Ananthapadmanabhan et al. |
| 7,776,347 B2 | 8/2010 | Kerschner et al. |
| 8,252,271 B2 | 8/2012 | Singer et al. |
| 8,349,301 B2 | 1/2013 | Wells et al. |
| 8,349,302 B2 | 1/2013 | Johnson et al. |
| 8,361,448 B2 | 1/2013 | Johnson et al. |
| 8,361,449 B2 | 1/2013 | Wells et al. |
| 8,361,450 B2 | 1/2013 | Johnson et al. |
| 8,367,048 B2 | 2/2013 | Wells et al. |
| 8,470,305 B2 | 6/2013 | Johnson et al. |
| 8,635,014 B2 | 1/2014 | Jung |
| 8,653,014 B2 | 2/2014 | Hilvert et al. |
| 8,655,819 B1 | 2/2014 | Burkard et al. |
| 8,663,612 B2 | 3/2014 | Gamez-Garcia et al. |
| 8,901,062 B2 | 12/2014 | De Meirleir et al. |
| 8,932,569 B2 | 1/2015 | Garrison et al. |
| 8,940,285 B2 | 1/2015 | Leray et al. |
| 9,005,585 B2 | 4/2015 | Deckner et al. |
| 9,138,429 B2 | 9/2015 | Wise et al. |
| 9,381,382 B2 | 6/2016 | Schwartz et al. |
| 9,393,188 B2 | 7/2016 | Deckner et al. |
| 9,587,209 B2 | 3/2017 | De Meirleir et al. |
| 2001/0047039 A1 | 11/2001 | Mcmanus |
| 2002/0119113 A1 | 8/2002 | Ellis |
| 2002/0131946 A1 | 9/2002 | Pham et al. |
| 2002/0169283 A1 | 11/2002 | Lu |
| 2002/0183300 A1 | 12/2002 | Fliss |
| 2003/0012646 A1 | 1/2003 | Liao |
| 2003/0044471 A1 | 3/2003 | Sakuma |
| 2003/0095938 A1 | 5/2003 | Casero |
| 2003/0119806 A1 | 6/2003 | Lindell |
| 2003/0130145 A1 | 7/2003 | Patel |
| 2003/0138497 A1 | 7/2003 | Sakuma |
| 2003/0171231 A1 | 9/2003 | Shana |
| 2003/0185779 A1 | 10/2003 | Mitsumatsu |
| 2003/0215522 A1 | 11/2003 | Johnson |
| 2003/0223952 A1 | 12/2003 | Wells et al. |
| 2003/0224954 A1 | 12/2003 | Wells et al. |
| 2003/0224955 A1 | 12/2003 | Ribery |
| 2004/0058855 A1 | 3/2004 | Schwartz |
| 2004/0092897 A1 | 5/2004 | Macedo Jr. |
| 2004/0157754 A1 | 8/2004 | Geary et al. |
| 2004/0167114 A1 | 8/2004 | Fliss |
| 2004/0191331 A1 | 9/2004 | Schwartz |
| 2004/0197294 A1 | 10/2004 | Seipel |
| 2004/0223941 A1 | 11/2004 | Schwartz |
| 2004/0234471 A1 | 11/2004 | Corbella |
| 2004/0266886 A1 | 12/2004 | Seipel |
| 2005/0031569 A1 | 2/2005 | Seipel |
| 2005/0112083 A1 | 5/2005 | Wells et al. |
| 2005/0143268 A1 | 6/2005 | Midha |
| 2005/0181067 A1 | 8/2005 | Yokoyama |
| 2005/0196368 A1 | 9/2005 | Laurent et al. |
| 2005/0202984 A1 | 9/2005 | Schwartz |
| 2005/0267258 A1 | 12/2005 | Rajaraman et al. |
| 2006/0024256 A1 | 2/2006 | Wells |
| 2006/0024381 A1 | 2/2006 | Schwartz |
| 2006/0025256 A1 | 2/2006 | Wake |
| 2006/0045861 A1 | 3/2006 | Bejger |
| 2006/0078524 A1 | 4/2006 | Midha et al. |
| 2006/0078527 A1 | 4/2006 | Midha et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0250658 A1 | 11/2006 | Jurgensen |

(56) References Cited

U.S. PATENT DOCUMENTS

| | | | |
|---|---|---|---|
| 2006/0251605 A1 | 11/2006 | Belmar | |
| 2006/0269501 A1 | 11/2006 | Johnson | |
| 2006/0269502 A1 | 11/2006 | Johnson | |
| 2007/0110696 A1* | 5/2007 | Johnson | A61K 8/0295 424/70.13 |
| 2007/0110700 A1 | 5/2007 | Wells | |
| 2008/0039352 A1 | 2/2008 | Wells et al. | |
| 2008/0096786 A1 | 4/2008 | Holt et al. | |
| 2008/0152611 A1 | 6/2008 | Wells | |
| 2008/0187507 A1 | 8/2008 | Johnson | |
| 2010/0061952 A1 | 3/2010 | Wells et al. | |
| 2010/0226868 A1 | 9/2010 | Gamez-Garcia et al. | |
| 2010/0234260 A1 | 9/2010 | Sekine et al. | |
| 2010/0322878 A1 | 12/2010 | Stella et al. | |
| 2010/0330018 A1 | 12/2010 | Lorant et al. | |
| 2011/0053818 A1 | 3/2011 | Chuchotiros et al. | |
| 2011/0065624 A1 | 3/2011 | Boutique et al. | |
| 2011/0067720 A1 | 3/2011 | Ranade et al. | |
| 2011/0070180 A1 | 3/2011 | Ranade et al. | |
| 2011/0081392 A1 | 4/2011 | de Arruda et al. | |
| 2011/0110991 A1 | 5/2011 | Garrison et al. | |
| 2012/0164198 A1 | 6/2012 | Johnson et al. | |
| 2012/0308502 A1 | 12/2012 | Wise et al. | |
| 2012/0329768 A1 | 12/2012 | Wise et al. | |
| 2013/0090279 A1 | 4/2013 | Hilvert et al. | |
| 2013/0131188 A1 | 5/2013 | Beckedahl et al. | |
| 2013/0174863 A1 | 7/2013 | Marsh et al. | |
| 2013/0243717 A1 | 9/2013 | Catalan et al. | |
| 2013/0243835 A1 | 9/2013 | Tanner et al. | |
| 2014/0018276 A1 | 1/2014 | Coffindaffer et al. | |
| 2014/0099276 A1* | 4/2014 | Yang | A61K 8/8152 424/70.16 |
| 2014/0162931 A1 | 6/2014 | De Meirleir et al. | |
| 2015/0011450 A1 | 1/2015 | Carter et al. | |
| 2015/0059795 A1 | 3/2015 | Vatter | |
| 2015/0093422 A1 | 4/2015 | Garrison et al. | |
| 2015/0342842 A1 | 12/2015 | Wise et al. | |
| 2016/0106663 A1 | 4/2016 | Gulbin | |
| 2017/0216158 A1 | 8/2017 | Deckner et al. | |
| 2017/0333734 A1 | 11/2017 | Mauer et al. | |
| 2017/0367955 A1 | 12/2017 | Brown et al. | |
| 2018/0071185 A1 | 3/2018 | Cochran et al. | |
| 2018/0098923 A1 | 4/2018 | Hutton, III | |
| 2020/0188243 A1 | 6/2020 | Brown | |

FOREIGN PATENT DOCUMENTS

| | | |
|---|---|---|
| CN | 10532660 B | 4/2018 |
| EP | 0037318 A1 | 10/1981 |
| EP | 0077630 A1 | 4/1983 |
| EP | 0627216 A2 | 12/1994 |
| EP | 1123693 A2 | 8/2001 |
| EP | 1066024 B1 | 10/2002 |
| FR | 2593801 B1 | 5/1986 |
| GB | 3B849433 A1 | 9/1960 |
| GB | 2177108 B | 7/1989 |
| JP | 5209881 A | 8/1977 |
| JP | 06134227 A | 5/1994 |
| JP | 07179887 A | 11/1994 |
| JP | H07118103 A | 5/1995 |
| JP | 2001181145 A | 7/2001 |
| JP | 2002104940 A | 4/2002 |
| JP | 2004262805 A | 9/2004 |
| JP | 2004292387 A | 10/2004 |
| JP | 2004292390 A | 10/2004 |
| JP | 2004307463 | 11/2004 |
| JP | 2005022983 | 1/2005 |
| JP | 2005187342 | 7/2005 |
| JP | 4016238 B2 | 9/2007 |
| JP | 4069228 B2 | 1/2008 |
| JP | 4129645 B2 | 5/2008 |
| WO | WO9308787 A1 | 5/1993 |
| WO | WO9410973 A1 | 5/1994 |
| WO | WO9625144 A1 | 8/1996 |
| WO | WO9625913 A1 | 8/1996 |
| WO | WO9726854 A1 | 7/1997 |
| WO | WO9847372 A1 | 10/1998 |
| WO | WO9938489 A1 | 8/1999 |
| WO | WO9959540 A1 | 11/1999 |
| WO | WO0100149 A1 | 1/2001 |
| WO | WO0117492 A1 | 3/2001 |
| WO | WO0139735 A1 | 6/2001 |
| WO | WO0222091 A2 | 3/2002 |
| WO | WO02076422 A1 | 10/2002 |
| WO | WO2004022681 A1 | 3/2004 |
| WO | WO2004022682 A1 | 3/2004 |
| WO | WO2010006866 A1 | 1/2010 |
| WO | WO2010034736 A1 | 4/2010 |
| WO | WO2011120799 A1 | 10/2011 |
| WO | WO2011134832 A2 | 11/2011 |
| WO | 2012138696 A2 | 10/2012 |
| WO | WO2012175677 A2 | 12/2012 |
| WO | WO20121756821 A2 | 12/2012 |
| WO | 2017088459 A1 | 6/2017 |

OTHER PUBLICATIONS

Eccleston, G.M., Application of Emulsion Stability Theories to Mobile and Semisolid o/w Emulsions, Cosmetics Magazine, vol. 101, 1986.

Eccleston, G.M., Application of Emulsion Theory to Complex and Real Systems, International Journal of Cosmetic Science, 1985.

Eccleston, G.M., Formulating Cosmetic Emulsions, Cosmetics Magazine, vol. 112, 1997.

Eccleston, G.M., Functions of Mixed Emulsifiers and Emulsifying Waxes in Dermatological Lotions and Creams, Colloids and Surfaces, vol. 123, 1997.

Eccleston, G.M., Microstructural Changes During Storage of Cetostearyl Alcohol/Polyoxyethylene Alkyl Ether Surfactants, University of Strathclyde, 1988.

Eccleston, G.M., Multiple Phase Oil and Water Emulsions, Journal of Cosmetic Chemists, 1990.

Eccleston, G.M., Structure and Rheology of Semisolid o/w Creams Containing Cetyl Alcohol/Non-ionic Surfactant Mixed Emulsifier and Different Polymers, International Journal of Cosmetic Science, 2004.

Eccleston, G.M., Synchrotron X-ray Investigations into the Lamellar Gel Phase Formed in Creams Prepared with Fatty Alcohols, International Journal of Pharmaceuticals, 2000.

Eccleston, G.M., The Influence of Fatty Alcohols on the Structure and Stability of Creams Preapred with Fatty Alcohols, International Journal of Cosmetic Science, 1982.

All final and non-final office actions for U.S. Appl. No. 13/646,227 (P&G Case 12355M).

All final and non-final office actions for U.S. Appl. No. 14/322,573 (P&G Case 12988M).

All final and non-final office actions for U.S. Appl. No. 14/478,013 (P&G Case 13045).

All final and non-final office actions for U.S. Appl. No. 14/881,714 (P&G Case 13592).

All final and non-final office actions for U.S. Appl. No. 15/703,046 (P&G Case 14504M).

All final and non-final office actions for U.S. Appl. No. 15/728,663 (P&G Case 14529).

Barry & Rowe, The Characterization by Small Angle X-Ray Scattering of a Gel with a Lamellar Structure, International Journal of Pharmaceuticals, 1989.

Barry & Saunders, Kinetics of Structure Build-up in Self Bodied Emulsions Stabalized by Mixed Emulsifiers, Journal of Colloid Science, vol. 41, 1972.

Barry, B.W., Structure and Rheology of Emulsions Stabalized by Mixed Emulsifiers, British Society of Rheology, 1970.

Benton et al, Phase Behavior and Network Formation in a Cationic Surfactant-Fatty Alcohol System, JAOCS, vol. 64, 1987.

Burgess, J.D., Practical Analysis of Complex Coacervate Systems, Journal of Colloid Science, vol. 140, 1990.

(56) References Cited

OTHER PUBLICATIONS

CTFA Cosmetic Ingredient Dictionary, 1982, 3rd Edition, The Cosmetic, Toiletry & Fragrance Association, Inc., Washington, DC (book not included).
Encyclopedia of Polymer Science and Engineering, John Wiley & Sons, vol. 15, 1989 (book not included).
Griffin, W.C., Calculation of HLB Values of Non-Ionic Surfactants, Journal of the Society of Cosmetic Chemists; 1954. vol. 5, pp. 249-235.
Korhonen et al, Rheological Properties of Three Component Creams Containing Sorbitan Monoesters as Surfactants, International Journal of Pharmaceuticals, 2002.
Louden et al, A Preliminary Examination of the Structure of Gels and Emulsions Containing Cetostearyl Alcohol, International Journal of Pharmaceuticals, 1985.
McCutcheon, Emulsifiers and Detergents, MC Pub Company, 1989 (book not included).
Meirleir Niels De et al., "The rheological properties of hydrogenated castor oil crystals", Colloid & Polymer Science, Springer Verlag, Heidelberg, DE, vol. 292, No. 10, Jun. 12, 2014, pp. 2539-2547.
Momentive SFE839 product brochure, https://www.momentive.com/products/showtechnicaldatasheet.aspx?id=14443available Sep. 2008; accessed Jul. 17, 2015.
Noll, W., Chemistry and Technology of Silicones, Academic Press, 1968 (book not included).
Patel et al, Properties of Cetrimide / Cetostearyl Alcohol Ternary Gels; Preparation Effects, International Journal of Pharmaceuticals, 1985.
PCT International Search Report and Written Opinion for PCT/US2014/045197 dated Oct. 7, 2014.
PCT International Search Report and Written Opinion for PCT/US2014/054294 dated Nov. 11, 2014.
PCT International Search Report and Written Opinion for PCT/US2015/056423 dated Jan. 8, 2016.
PCT International Search Report and Written Opinion for PCT/US2017/039444 dated Aug. 28, 2017.
PCT International Search Report and Written Opinion for PCT/US2017/051249 dated Nov. 10, 2017.
PCT International Search Report and Written Opinion for PCT/US2017/055821 dated Dec. 6, 2017.
Savic et al, Colloidal Microstructure of Binary Systems and Model Creams Stabilized with an Alkylpolyglucoside Emulsifier, Colloid Polymer Science, vol. 283, 2004.
Saxton, C., Antiplaque Effects and Mode of Action of a Combination of Zinc Citrate and a Nonionic Antimicrobial Agent, Scandinavian Journal, vol. 96, 1988.
Suzuki et al, Secondary Droplet Emulsion: Mechanism & Effects of Liquid Crystal Formation in o/w Emulsion, Journal of Dispersion Science, 1984.
Van Cutsem, Journal of the American Academy of Dermatology, XP-002288119, 1998.
Van Oss, C.J., Coacervation, Complex Coacervation and Flocculation, Journal of Dispersion Science, vol. 9, 1989.
Yoon et al, A Study of Gel Structure in the Nonionic Surfactant / Cetostearyl Alcohol / Water Ternary Systems by Differential Scanning Calorimeter, Journal of Dispersion Science, 1999.
U.S. Appl. No. 16/907,711, filed Jun. 22, 2020, Dunlop et al.
U.S. Appl. No. 16/902,629, filed Jun. 16, 2020, Cochran et al.
"Polyelectrolyte-Micelle—Coacervation—Effect of coacervate on the properties of shampoo", Yoshiko Kiwatari et al., J. Soc. Cosmet. Chem. Japan, vol. 38, No. 3, 2004, pp. 211-219.
All final and non-final office actions for U.S. Appl. No. 16/713,142 (P&G Case 15428).
All final and non-final office actions for U.S. Appl. No. 16/902,629 (P&G Case 14504MD).
All final and non-final office actions for U.S. Appl. No. 16/907,711 (P&G Case 15586).
PCT International Search Report and Written Opinion for PCT/US2019/065452 dated Mar. 20, 2020.

\* cited by examiner

SHAMPOO COMPOSITION CONTAINING A GEL NETWORK

FIELD OF THE INVENTION

The present invention relates to a shampoo composition containing a dispersed gel network phase.

BACKGROUND OF THE INVENTION

Human hair becomes soiled due to its contact with the surrounding environment and from the sebum secreted by the scalp, in addition to the use of third-step stylers and hair treatments that leave a visually or tactilely noticeable residue behind on the hair. The soiling of hair causes it to have a dirty feel and an unattractive appearance, necessitating shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils. Conditioners are subsequently employed to "fix" the hair, enabling sufficient conditioning of the hair to allow easier removal of tangles left by the shampoo.

A variety of approaches have been employed to alleviate the aforementioned after-shampoo problems. One approach is the application of hair shampoos which attempt to both cleanse and condition the hair from a single product. Another approach is the practice of "co-washing", where shampooing is replaced with the use of a cleansing conditioner to clean and effectively conditioner the hair. A third approach is switching the order of product application, wherein conditioner is applied prior to shampooing, requiring the consumer to alter her natural habits and practices to achieve the desired hair benefits.

In order to provide hair conditioning benefits from a cleansing shampoo base, a wide variety of conditioning actives have been proposed. Traditionally, shampoos have used cationic polymers to form coacervate for conditioning benefits. However, these shampoo compositions generally do not deliver satisfactory smooth feel in dry hair. The use of cleansing conditioners may clean and condition the hair, however the typical elements of the shampoo experience that signal clean hair, such as abundant lather, are sacrificed.

The use of shampoo compositions comprising a dispersed fatty alcohol gel network phase have been proposed to achieve improved wet feel and dry conditioning benefit while not interfering with cleansing efficacy. However, it was previously believed that increasing the conditioning agents included in the fatty alcohol gel network phase to higher levels would impact the lathering of the shampoo formulation. This could impact the ability of the shampoo to adequately clean the hair. Additionally, higher gel network levels may render the product phase-unstable.

Based on the foregoing, there is a need for a shampoo that effectively cleans and conditions hair which exhibits a product rheology that is more conditioner-like to aid product phase stability and more holistically communicate the conditioning benefits therein, while still providing a shampoo-like lather profile for signaling cleaning.

SUMMARY OF THE INVENTION

A shampoo composition comprising a dispersed gel network phase comprising: from about 2.8 weight % to about 8 wt % of one or more fatty alcohols, by weight of said shampoo composition; at least 0.01% of one or more secondary surfactants by weight of said shampoo composition, wherein the secondary surfactant comprises sodium laureth-n sulfate wherein n is from about 0 to about 5; and water; and from about 5% to about 50% of a detersive surfactant, by weight of said shampoo composition; from about 0.02% to about 1.50% of a material, by weight of said shampoo composition, selected from the group consisting of structurants, suspending agents and mixtures thereof, from about 0.5 to about 1% of a cationic deposition polymer, by weight of said shampoo composition; at least 20% of an aqueous carrier, by weight of said shampoo composition.

A method of making a shampoo composition comprising: forming a dispersed gel network phase by combining from about 2.8 weight % to about 8 wt % of one or more fatty alcohols, by weight of said shampoo composition; at least 0.01% of one or more secondary surfactants by weight of said shampoo composition, wherein the secondary surfactant comprises sodium laureth-n sulfate wherein n is from about 0 to about 5; and water; and mixing the dispersed gel network phase into a shampoo base comprising: from about 5% to about 50% of a detersive surfactant by weight of said shampoo composition; from about 0.02% to about 1.50% of hydrogenated castor oil by weight of said shampoo composition; from about 0.5 to about 1% by weight of a cationic deposition polymer; at least 20% of an aqueous carrier, by weight of said shampoo composition.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
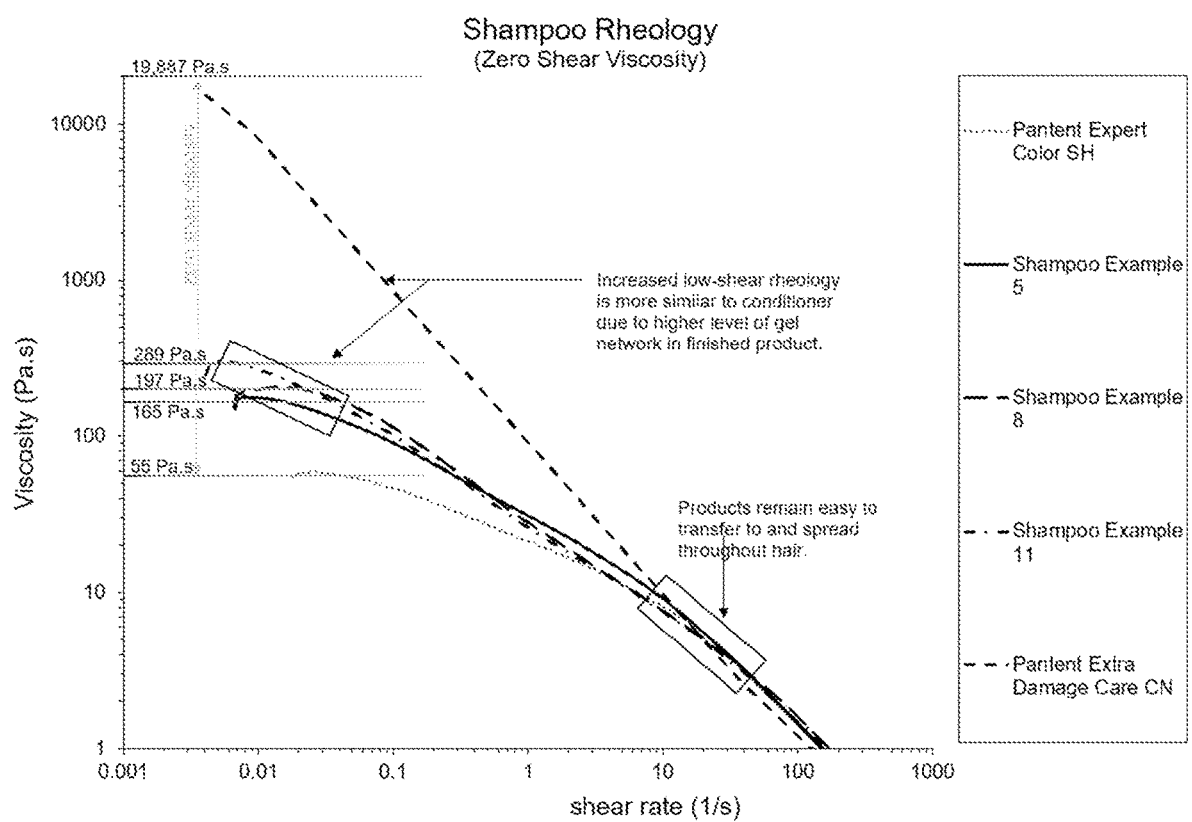
FIG. 1 is a graph of shampoo rheology.
Figure 2:
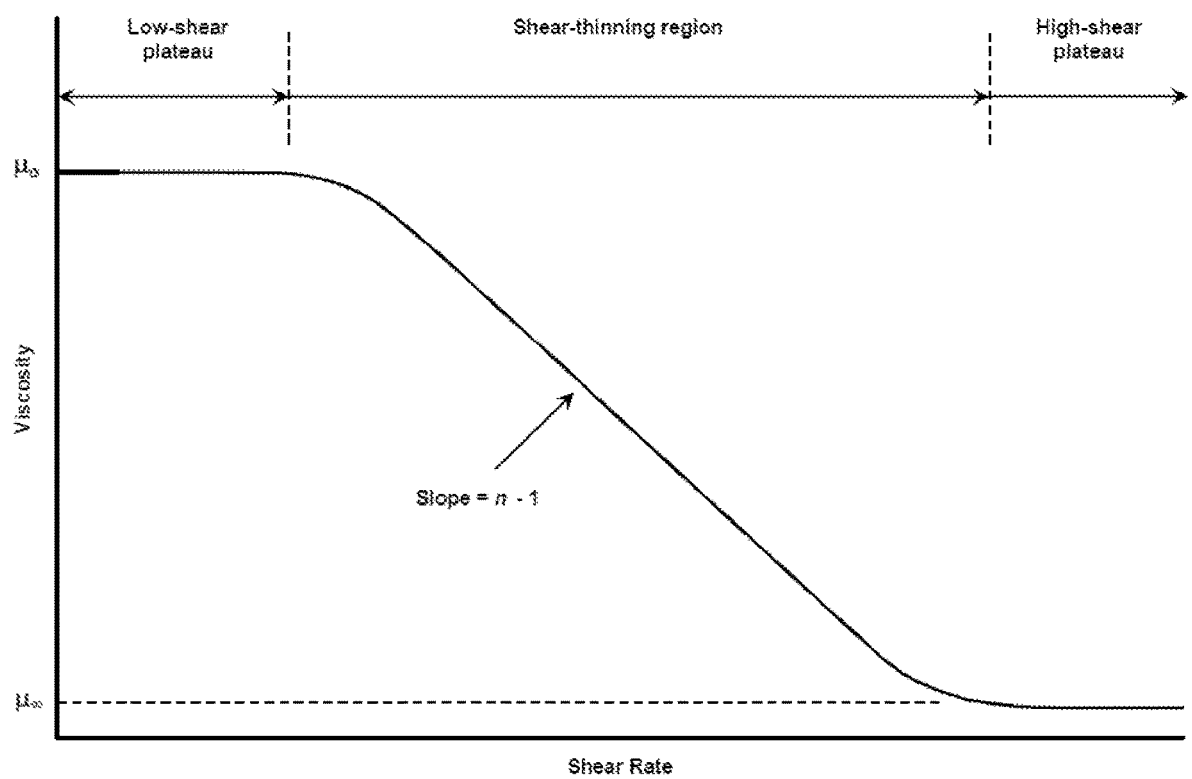
FIG. 2 is a graph of shampoo rheology.

While the specification concludes with claims which particularly point out and distinctly claim the invention, it is believed the present invention will be better understood from the following description.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

The term "charge density," as used herein, refers to the ratio of the number of positive charges on a polymer to the molecular weight of said polymer.

The term "molecular weight" or "Molecular weight" refers to the weight average molecular weight unless otherwise stated. Molecular weight is measured using industry standard method, gel permeation chromatography ("GPC").

The term "comprising," as used herein, means that other steps and other ingredients which do not affect the end result can be added. This term encompasses the terms "consisting of" and "consisting essentially of." The compositions and methods/processes of the present invention can comprise, consist of, and consist essentially of the elements and limitations of the invention described herein, as well as any of the additional or optional ingredients, components, steps, or limitations described herein.

The term "polymer," as used herein, includes materials whether made by polymerization of one type of monomer or made by two (i.e., copolymers) or more types of monomers.

The term "suitable for application to human hair," as used herein, means that the compositions or components thereof so described are acceptable for use in contact with human hair and the scalp and skin without undue toxicity, incompatibility, instability, allergic response, and the like.

The term "water soluble," as used herein, means that the material is soluble in water in the present composition. In general, the material should be soluble at 25° C. at a concentration of 0.1% by weight of the water solvent, alternatively at 1%, alternatively at 5%, and alternatively at 15%.

Shampoo Composition

As used herein, the term "dispersed gel network" or "gel network" refers to a lamellar or vesicular solid crystalline phase which comprises at least one fatty alcohol, at least one secondary surfactant, and water and/or other suitable solvents. This dispersed gel network is further combined with a shampoo base comprising a detersive surfactant, such as an anionic surfactant, hydrogenated castor oil, and one or more cationic polymers to form a shampoo product.

Dispersed Gel Network

The shampoo composition of the present invention comprises a dispersed gel network comprising one or more fatty alcohols. The dispersed gel network is included in shampoo compositions of the present invention to provide conditioning benefits. As used herein, the term "gel network" refers to a lamellar or vesicular solid crystalline phase which comprises at least one fatty alcohol as specified below, at least one secondary surfactant as specified below, and water and/or other suitable solvents. The lamellar or vesicular phase comprises bi-layers made up of a first layer comprising the fatty alcohol and the secondary surfactant and alternating with a second layer comprising the water or other suitable solvent. The term "solid crystalline", as used herein, refers to the structure of the lamellar or vesicular phase which forms at a temperature below the melt transition temperature of the layer in the gel network comprising the one or more fatty alcohols.

Gel networks which comprise, for example, fatty alcohols have been used for years in cosmetic creams and hair conditioners. Such cosmetic creams and hair conditioners, however, typically contain very low amounts, if any, of detersive surfactant. Thus, such known products do not provide a combination of cleansing and conditioning to the hair or skin.

Gel networks, generally, are further described by G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International, Vol. 7*, 63-70 (1986). In an embodiment of the present invention, the dispersed gel network phase is pre-formed. The term "pre-formed", as used herein, means that at least fifty percent of the mixture of the fatty alcohol, secondary surfactant, and water or other suitable solvent is substantially a solid crystalline phase when added to the other components of the shampoo composition.

The gel network as described herein is prepared as a separate pre-mix, which, after being cooled, is subsequently incorporated with the detersive surfactant and the other components of the shampoo composition. Preparation of the gel network component is discussed in more detail below in the section entitled Process of Making a Shampoo Composition as well as in the Examples.

The cooled and pre-formed gel network component subsequently is added to the other components of the shampoo composition, including the detersive surfactant component. While not intending to be limited by theory, it is believed that incorporation of the cooled and pre-formed gel network component with the detersive surfactant and other components of the shampoo composition allows the formation of a substantially equilibrated lamellar dispersion ("ELD") in the final shampoo composition. The ELD is a dispersed lamellar or vesicular phase resulting from the pre-formed gel network component substantially equilibrating with the detersive surfactants, water, and other optional components, such as salts, which may be present in the shampoo composition. This equilibration occurs upon incorporation of the pre-formed gel network component with the other components of the shampoo composition and is effectively complete within about 24 hours after making. Shampoo compositions in which the ELD is formed provide hair with improved wet and dry conditioning benefits.

For purposes of clarification, as used herein, the term "ELD" refers to the same component of the shampoo compositions of the present invention as the phrase "dispersed gel network phase".

The presence of the gel network in the pre-mix and in the final shampoo composition in the form of the ELD can be confirmed by means known to one of skill in the art, such as X-ray analysis, optical microscopy, electron microscopy, and differential scanning calorimetry. A method of differential scanning calorimetry is described below. For methods of X-ray analysis, see U.S. 2006/0024256 A1.

The scale size of the dispersed gel network phase in the shampoo composition (i.e., the ELD) can range from about 10 nm to about 500 nm. The scale size of the dispersed gel network phase in the shampoo composition can range from about 0.5 μm to about 10 μm. Alternatively, the scale size of the dispersed gel network phase in the shampoo composition can range from about 10 μm to about 150 μm.

The scale size distribution of the dispersed gel network phase in the shampoo composition may be measured with a laser light scattering technique, using a Horiba model LA 910 Laser Scattering Particle Size Distribution Analyzer (Horiba Instruments, Inc. Irvine Calif., USA). The scale size distribution in a shampoo composition of the present invention may be measured by combining 1.75 g of the shampoo composition with 30 mL of 3% $NH_4Cl$, 20 mL of 2% $Na_2HPO_4.7H_2O$, and 10 mL of 1% laureth-7 to form a mixture. This mixture is then stirred for 5 minutes. As appropriate for the individual Horiba instrument being used, samples in the range of 1 to 40 mL are taken and then injected into the Horiba instrument, which contains 75 mL of 3% $NH_4Cl$, 50 mL of 2% $Na_2HPO_4.7H_2O$, and 25 mL of 1% laureth-7, until the Horiba instrument reading is between 88-92% T, which is needed for the scale size measurement.

Once this is achieved, a measurement is taken after 2 minutes of circulation through the Horiba instrument to provide the scale size measurement. A subsequent measurement is taken using a sample of the shampoo composition which has been heated above the melt transition temperature of all fatty materials present in the shampoo composition, such that the gel network component is melted. This subsequent measurement allows a scale size distribution to be taken of all of the remaining materials in the shampoo, which then can be compared to the scale size distribution of the first sample and assist in the analysis.

A. Fatty Alcohol

The gel network component of the present invention comprises at least one fatty alcohol. Individual fatty alcohol compounds or combinations of two or more different fatty alcohol compounds may be selected.

Fatty alcohols suitable for use in the present invention are those having from about 16 to about 70 carbon atoms, alternatively from about 16 to about 60 carbon atoms, alternatively from about 16 to about 50 carbon atoms, alternatively from about 16 to about 40 carbon atoms, and alternatively from about 16 to about 22 carbon atoms. These fatty alcohols may be straight or branched chain alcohols and may be saturated or unsaturated. Non-limiting examples of suitable fatty alcohols include stearyl alcohol, arachidyl alcohol, behenyl alcohol, C21 fatty alcohol (1-heneicosanol), C23 fatty alcohol (1-tricosanol), C24 fatty alcohol (lignoceryl alcohol, 1-tetracosanol), C26 fatty alcohol (1-hexacosanol), C28 fatty alcohol (1-octacosanol), C30 fatty alcohol (1-triacontanol), C20-40 alcohols (e.g., Performacol 350 and 425 Alcohols, available from New Phase Technologies), C30-50 alcohols (e.g., Performacol 550 Alcohol), C40-60 alcohols (e.g., Performacol 700 Alcohol), cetyl alcohol, and mixtures thereof.

Mixtures of different fatty alcohols comprising one or more fatty alcohols having from about 16 to about 70 carbon atoms may also comprise some amount of one or more fatty alcohols or other fatty amphiphiles which have less than about 16 carbon atoms or greater than about 70 carbon atoms and still be considered to be within the scope of the present invention, provided that the resulting dispersed gel network phase has a melt transition temperature of at least about 25° C., alternatively at least about 28° C., alternatively at least about 31° C., alternatively at least about 34° C., and alternatively at least about 37° C.

Such fatty alcohols suitable for use in the present invention may be of natural or vegetable origin, or they may be of synthetic origin.

The shampoo compositions of the present invention comprise fatty alcohol as part of the dispersed gel network phase in an amount of at least about 2.8%, alternatively from about 2.8% to about 14%, alternatively from about 2.8% to about 16%, alternatively from about 2.8% to about 5%, alternatively from about 3% to about 10%, and alternatively from about 3% to about 8%, by weight of the shampoo composition.

In an embodiment of the present invention, the weight ratio of the fatty alcohol to the secondary surfactant in the gel network component is greater than about 1:9, alternatively from about 1:5 to about 100:1, and alternatively from about 1:1 to about 50:1.

B. Secondary Surfactant

The gel network component of the present invention also comprises a secondary surfactant. As used herein, "secondary surfactant" refers to one or more surfactants which are combined with the fatty alcohol and water to form the gel network of the present invention as a pre-mix separate from the other components of the shampoo composition. The secondary surfactant is separate from and in addition to the detersive surfactant component of the shampoo composition. However, the secondary surfactant may be the same or different type of surfactant or surfactants as that or those selected for the detersive surfactant component described above.

The shampoo compositions of the present invention comprise secondary surfactant as part of the pre-formed dispersed gel network phase in an amount from about 0.01% to about 15%, alternatively from about 0.1% to about 10%, and alternatively from about 0.2% to about 5%, by weight of the shampoo composition.

Suitable secondary surfactants include anionic, zwitterionic, amphoteric, cationic, and nonionic surfactants. The secondary surfactant may be selected from anionic, cationic, and nonionic surfactants, and mixtures thereof. For additional discussion of secondary surfactants which are suitable for use in the present invention, see U.S. 2006/0024256 A1.

Additionally, certain secondary surfactants which have a hydrophobic tail group with a chain length of from about 16 to about 22 carbon atoms. For such secondary surfactants, the hydrophobic tail group may be alkyl, alkenyl (containing up to 3 double bonds), alkyl aromatic, or branched alkyl. the secondary surfactant may be present in the gel network component relative to the fatty alcohol at a weight ratio from about 1:5 to about 5:1. SLE1S may be particularly useful as SLE1S is a very efficient surfactant which foams well. In a shampoo composition with high levels of conditioning actives, SLE1S may further provide enhanced lather and cleaning.

Mixtures of more than one surfactant of the above specified types may be used for the secondary surfactant of the present invention.

C. Water or Suitable Solvents

The gel network component of the present invention also comprises water or suitable solvents. The water or suitable solvent and the secondary surfactant together contribute to the swelling of the fatty alcohol. This, in turn, leads to the formation and the stability of the gel network. As used herein, the term "suitable solvent" refers to any solvent which can be used in the place of or in combination with water in the formation of the gel network of the present invention.

The shampoo compositions of the present invention comprise water or suitable solvents as part of the pre-formed dispersed gel network phase in an amount suitable to achieve a gel network when combined with fatty alcohol and secondary surfactant according to the present invention.

The shampoo compositions may comprise as part of the pre-formed dispersed gel network phase at least about 0.05% of water or a suitable solvent, by weight of the shampoo composition.

The shampoo compositions may comprise water or a suitable solvent as part of the pre-formed dispersed gel network phase is an amount relative to the amount of fatty alcohol at a weight ratio of at least about 1:1.

Shampoo Base

The dispersed gel network phase is then dispersed into a shampoo base. The shampoo base can comprise a cationic deposition polymer, a surfactant, a co-surfactant, an aqueous carrier and additional components. The resulting shampoo compositions can be substantially free of silicones. As used here in substantially free of silicone means the level of silicone compound is, if included, 0.1% or less, alternatively 0.05% or less, alternatively 0.01% or less, and alternatively 0%.

Cationic Deposition Polymer

The shampoo compositions of the present invention may include a cationic deposition polymer. The cationic deposition polymer is included to effectively enhance deposition of the gel network component. The cationic deposition polymer can comprise any cationic polymer that enhances the deposition of the gel network from the shampoo onto the hair and/or scalp.

The concentration of the deposition aid in the shampoo composition should be sufficient to effectively enhance the deposition of the gel network component and ranges from about 0.05% to about 5%, alternatively from about 0.075% to about 2.5%, alternatively from about 0.1% to about 1.0%, and alternatively from about 0.5% to about 1.0% by weight of the shampoo composition.

Suitable cationic deposition polymers may have cationic charge densities of at least about 0.4 meq/g, alternatively at least about 0.7 meq/g, alternatively at least about 1.2 meq/g, alternatively at least about 1.5 meq/g, alternatively less than about 7 meq/g, and alternatively less than about 5 meq/g, at the pH of intended use of the composition. The pH will generally range from about pH 3 to about pH 9, alternatively between about pH 4 and about pH 8. The "cationic charge density" of a polymer, as that term is used herein, refers to the ratio of the number of positive charges on the polymer to the molecular weight of the polymer. The weight average molecular weight of such suitable cationic polymers will generally be between about 10,000 and 10 million, alternatively between about 50,000 and about 5 million, and alternatively between about 100,000 and about 3 million.

Suitable cationic polymers for use in the composition include polysaccharide polymers, such as cationic cellulose derivatives and cationic starch derivatives, such as salts of hydroxyethyl cellulose reacted with trimethyl ammonium substituted epoxide. Other suitable cationic polymers include cationic guar gum derivatives, such as guar hydroxypropyltrimonium chloride. Further suitable cationic polymers include galactomannan polymer derivatives having a mannose to galactose ratio of greater than 2:1 on a monomer to monomer basis, such as cassia gum hydroxypropyltrimonium chloride. Particularly suitable cationic deposition polymers include guar hydroxypropyltrimonium chloride.

The cationic guar polymer may be formed from quaternary ammonium compounds. In an embodiment, the quaternary ammonium compounds for forming the cationic guar polymer conform to the general formula 1:

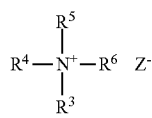

wherein where R3, R4 and R5 are methyl or ethyl groups; R6 is either an epoxyalkyl group of the general formula 2:

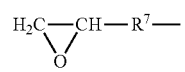

or R6 is a halohydrin group of the general formula 3:

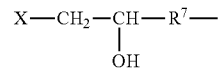

wherein R7 is a C1 to C3 alkylene; X is chlorine or bromine, and Z is an anion such as Cl—, Br—, I— or HSO4-.

In an embodiment, the cationic guar polymer conforms to the general formula 4:

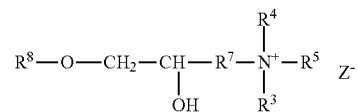

wherein R8 is guar gum; and wherein R4, R5, R6 and R7 are as defined above; and wherein Z is a halogen. In an embodiment, the cationic guar polymer conforms to Formula 5:

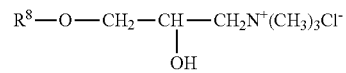

Suitable cationic guar polymers include cationic guar gum derivatives, such as guar hydroxypropyltrimonium chloride. In an embodiment, the cationic guar polymer is a guar hydroxypropyltrimonium chloride. Specific examples of guar hydroxypropyltrimonium chlorides include the Jaguar® series commercially available from Rhone-Poulenc Incorporated, for example Jaguar® C-17, which has a cationic charge density of about 0.6 meq/g and a M. Wt. of about 2.2 million g/mol and is available from Rhodia Company. Jaguar® C 13S which has a M. Wt. of 2.2 million g/mol and a cationic charge density of about 0.8 meq/g (available from Rhodia Company). N-Hance 3196, which has a charge density of about 0.7 and a M. Wt. Of about 1,100,000 g/mole and is available from ASI. BF-13, which is a borate (boron) free guar of charge density of about 1.1 meq/g and M. W.t of about 800,000 and BF-17, which is a borate (boron) free guar of charge density of about 1.7 meq/g and M. W.t of about 800,000 both available from ASI.

A combination of cationic polymers can improve the conditioning and lather of the shampoo composition. Using a cationic polymer with a charge density of from about 0.4 meq/g to about 0.8 meq/g, alternatively about 0.7 meq/g in combination with a cationic polymer having a molecular weight greater than about 1,000,000 can result in a shampoo composition with both lather stability and creaminess.

In one embodiment, the shampoo composition of the present invention comprises a combination of cationic guar and cationic polysaccharide deposition polymers wherein the respective weight ratio of guar to polysaccharide deposition polymers is greater than 2:1, alternatively wherein the weight ratio of guar to polysaccharide deposition polymers is greater than 3:1, and alternatively wherein the weight ratio of guar to polysaccharide deposition polymers is greater than 4:1.

In another embodiment, the shampoo composition of the present invention comprises a combination of cationic guar polymers only, wherein one cationic guar has a charge density of about 1.7 meq/g and another cationic guar has a molecular weight of about 1,100,000 g/mole.

In yet another embodiment, the shampoo composition of the present invention comprises a mixture of 3196 guar and BF-17 cationic guar, wherein the weight ratio of these two cationic deposition polymers is about 5:1, alternatively about 2:1, alternatively about 1:1, still alternatively about 1:2, and alternatively about 2:5 of 3196 to BF-17 respectively.

Detersive Surfactant

The shampoo composition of the present invention comprises one or more detersive surfactants in the shampoo base. The detersive surfactant component is included in shampoo compositions of the present invention to provide cleansing performance. The detersive surfactant may be selected from anionic detersive surfactant, zwitterionic, or amphoteric detersive surfactant, or a combination thereof. Such surfactants should be physically and chemically compatible with the components described herein, or should not otherwise unduly impair product stability, aesthetics or performance. Particularly suitable herein is sodium laureth-n-sulfate, wherein n=1 ("SLE1S"). SLE1S enables more efficient lathering and cleaning when compared to higher mole ethoxylate equivalents, especially in a shampoo composition that contains high levels of conditioning actives.

Suitable anionic detersive surfactant components for use in the composition herein include those which are known for use in hair care or other personal care shampoo compositions. In one embodiment, the anionic detersive surfactant may be a combination of sodium lauryl sulfate and sodium laureth-n sulfate. The concentration of the anionic surfactant component in the composition should be sufficient to provide the desired cleaning and lather performance, and generally range from about 5% to about 50%, alternatively from about 8% to about 30%, alternatively from about 9% to about 25%, and alternatively from about 10% to about 17%, by weight of the composition.

Suitable zwitterionic or amphoteric detersive surfactants for use in the composition herein include those which are known for use in hair care or other personal shampoo compositions. Concentration of such amphoteric detersive surfactants range from about 0.5% to about 20%, alternatively from about 1% to about 10%. Non-limiting examples of suitable zwitterionic or amphoteric surfactants are described in U.S. Pat. Nos. 5,104,646 and 5,106,609.

Additional anionic surfactants suitable for use herein include alkyl and alkyl ether sulfates of the formula $ROSO_3M$ and $RO(C_2H_4O)_xSO_3M$, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

Other suitable anionic surfactants include water-soluble salts of the organic, sulfonic acids of the general formula $[R^1—SO_3M]$. $R^1$ being a straight chain aliphatic hydrocarbon radical having from 13 to 17 carbon atoms, alternatively from 13 to 15 carbon atoms. M is a water soluble cation such as ammonium, sodium, potassium, and triethanolamine cation or salts of the divalent magnesium ion with two anionic surfactant anions. These materials are produced by the reaction of $SO_2$ and $O_2$ with suitable chain length normal paraffins ($C_{14}$-$C_{17}$) and are sold commercially as sodium paraffin sulfonates.

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth sulfate, sodium tridecyl sulfate, sodium methyl lauroyl taurate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

The shampoo composition of the present invention may further comprise additional surfactants for use in combination with the anionic detersive surfactant component described herein. Suitable additional surfactants include cationic and nonionic surfactants.

Non-limiting examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

Co-Surfactant

Co-surfactants are materials which are combined with the undecyl sulfate surfactant and optionally anionic surfactants to enhance lather volume and/or to modify lather texture. Typically these materials can be selected from a variety of families of structures including, but not limited to, amphoteric, zwitterionic, cationic, and nonionic. They are typically used with anionic surfactants in a weight ratio of 1:20 to 1:4, and alternatively in the 1:12 to 1:7 weight ratio.

The shampoo composition of the present invention may comprise from about 0.5 wt % to about 10 wt %, alternatively from about 0.5 wt % to about 5 wt %, alternatively from about 0.5 wt % to about 3 wt %, alternatively from about 0.5 wt % to about 2 wt %, and alternatively from about 0.5 wt % to about 1.75 wt % by weight of the composition of at least one suitable co-surfactant. The co-surfactant may serve to produce faster lather, facilitate easier rinsing, and/or mitigate harshness on the keratinous tissue. The co-surfactant further may aid in producing lather having more desirable texture, volume and/or other properties.

Amphoteric surfactants suitable for use herein include, but are not limited to derivatives of aliphatic secondary and tertiary amines in which the aliphatic radical can be straight or branched chain and wherein one substituent of the aliphatic substituents contains from about 8 to about 18 carbon atoms and one contains an anionic water solubilizing group, e.g., carboxy, sulfonate, sulfate, phosphate, or phosphonate. Examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378, and mixtures thereof.

In one embodiment the amphoteric surfactants may selected from the family of betaines such as lauryolamphoacetate.

Zwitterionic surfactants suitable for use herein include, but are not limited to derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Other zwitterionic surfactants suitable for use herein include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof. Other suitable amphoteric surfactants include amidobetaines and amidosulfobetaines, wherein the RCONH(CH$_2$)$_3$ radical, wherein R is a $C_{11}$-$C_{17}$ alkyl, is attached to the nitrogen atom of the betaine.

Nonionic co-surfactants typically used in the present composition for enhancing lather volume or texture include water soluble materials like lauryl dimethylamine oxide, cocodimethylamine oxide, cocoamidopropylamine oxide, laurylamidopropyl amine oxide, etc. or alkylpolyethoxylates like laureth-4 to laureth-7 and water insoluble components such as cocomonoethanol amide, cocodiethanol amide, lauroylmonoethanol amide, alkanoyl isopropanol amides, and fatty alcohols like cetyl alcohol and oleyl alcohol, and 2-hydroxyalkyl methyl ethers, etc.

Further suitable materials as co-surfactants herein include 1,2-alkylepoxides, 1,2-alkanediols, branched or straight chain alkyl glyceryl ethers (e.g., as disclosed in EP 1696023A1), 1,2-alkylcyclic carbonates, and 1,2-alkyl cyclicsulfites, particularly those wherein the alkyl group contains 6 to 14 carbon atoms in linear or branched configuration. Other examples include the alkyl ether alcohols derived from reacting C10 or C12 alpha olefins with ethylene glycol (e.g., hydroxyethyl-2-decyl ether, hydroxyethyl-2-dodecyl ether), as can be made according to U.S. Pat. Nos. 5,741,948; 5,994,595; 6,346,509; and 6,417,408.

Other nonionic surfactants may be selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

In a particular embodiment, the co-surfactant is selected from the group consisting of Cocomonoethanol Amide, Cocoamidopropyl Betaine, Laurylamidopropyl Betaine, Cocobetaine, lauryl betaine, lauryl amine oxide, sodium lauryl amphoacetate; alkyl glyceryl ethers, alkyl-di-glyceryl ethers, 1,2-alkyl cyclic sulfites, 1,2-alkyl cyclic carbonates, 1,2-alkyl-epoxides, alkyl glycidylethers, and alkyl-1,3-dioxolanes, wherein the alkyl group contains 6 to 14 carbon atoms in linear or branched configuration; 1,2-alkane diols where the total carbon content is from 6 to 14 carbon atoms linear or branched, methyl-2-hydroxy-decyl ethers, hydroxyethyl-2-dodecyl ether, hydroxyethyl-2-decyl ether, and mixtures thereof.

Cationic surfactants may be derived from amines that are protonated at the pH of the formulation, e.g. bis-hydroxyethyl lauryl amine, lauryl dimethylamine, lauroyl dimethyl amidoproplyl amine, cocoylamidopropyl amine, and the like. The cationic surfactants may also be derived from fatty quaternary ammonium salts such as lauryl trimethylammonium chloride and lauroylamidopropyl trimethyl ammonium chloride.

In one embodiment, the shampoo composition may comprise two or more phases to make a multiphase person care composition. One phase may comprise traditional personal care components, such as structured surfactants, and the second phase of multiphase personal care compositions of the present invention can comprise a benefit phase.

The benefit phase, when present, may be anhydrous and can be substantially free of water. The benefit phase can comprise less than about 5 wt % water, alternatively less than 3 wt % water, and alternatively less than 1 wt % water. The benefit phase can be substantially free of surfactant. The benefit phase can comprise less than about 5 wt % of surfactant, alternatively less than about 3 wt % of surfactant, and alternatively less than about 1 wt % surfactant.

The benefit phase may comprise hydrophobic moisturizing materials. The benefit phase can be comprised of the components selected from the group consisting of petrolatum, lanolin, hydrocarbon oils such as mineral oil, natural and synthetic waxes such as micro-crystalline waxes, paraffins, ozokerite, lanolin wax, lanolin alcohols, lanolin fatty acids, polyethylene, polybutene, polydecene and perhydrosqualene, volatile or non-volatile organosiloxanes and their derivatives such as dimethicones, cyclomethicones, alkyl siloxanes, polymethylsiloxanes and methylphenylpolysiloxanes, lanolin oil, esters such as isopropyl lanolate, acetylated lanolin, acetylated lanolin alcohols, lanolin alcohol linoleate, lanolin alcohol riconoleate natural and synthetic triglycerides such as castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, castor oil derivatives, sefoses, and combinations thereof.

In one embodiment, the benefit phase may comprise a hydrophobic moisturizing material. Hydrophobic moisturizing materials suitable for use in particular multi-phase compositions may have a Vaughan Solubility Parameter ("VSP") of from about 5 (cal/cm$^3$)$^{1/2}$ to about 15 (cal/cm$^3$)$^{1/2}$, as defined by Vaughan in Cosmetics and Toiletries, Vol. 103. Non-limiting examples of hydrophobic moisturizing materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988.

The shampoo composition of the present invention, when in a multiphase form, may comprise structured surfactant that is suitable for application to keratinous tissue such as skin and/or hair. The part of the shampoo composition which contains the structured surfactant can comprise in one embodiment at least about 50% of anisotropic phase, and in a different embodiment from about 50% to about 90% of an anisotropic phase. Structured surfactants may comprise anionic, nonionic, cationic, zwitterionic, amphoteric surfactants, soap, and combinations thereof, as disclosed herein and in US 2007/0248562 A1, in combination with a suitable structurant.

Alkylamphoacetates are suitable structured surfactants used in the multiphase compositions herein for improved product mildness and lather. The most commonly used alkylamphoacetates are lauroamphoacetate and cocoamphoacetate. Alkylamphoacetates can be comprised of monoacetates and diacetates. In some types of alkylamphoacetates, diacetates are impurities or unintended reaction products. However, the presence of diacetate can cause a variety of unfavorable composition characteristics when present in amounts over 15% of the alkylamphoacetates.

Suitable nonionic surfactants for use herein are those selected from the group consisting of glucose amides, alkyl polyglucosides, sucrose cocoate, sucrose laurate, alkanolamides, ethoxylated alcohols and mixtures thereof. In one embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

The structured surfactant may be in the form of a discrete structured domain, visibly distinct from the non-structured domain. Where the composition comprises both a structured and a non-structured phase, the structured domain can enable the incorporation of high levels of skin care actives that are not otherwise emulsified in the composition. In a particular embodiment the structured domain is an opaque structured domain. The opaque structured domain may be a lamellar phase, and may be a lamellar phase that produces a lamellar gel network.

In one embodiment, the structured surfactant is in the form of a lamellar phase, which provides resistance to shear, adequate yield to suspend particles and droplets, desirable rheology characteristics, and/or long term stability. The lamellar phase tends to have a viscosity that minimizes the need for viscosity modifiers.

Non-limiting examples of suitable structurants are described in U.S. Pat. No. 5,952,286, and include unsaturated and/or branched long chain ($C_8$-C24) liquid fatty acids or ester derivative thereof; unsaturated and/or branched long chain liquid alcohol or ether derivatives thereof, and mixtures thereof. The structured surfactant also may comprise short chain saturated fatty acids such as capric acid and caprylic acid. Without being limited by theory, it is believed that the unsaturated part of the fatty acid of alcohol or the branched part of the fatty acid or alcohol acts to "disorder" the surfactant hydrophobic chains and induce formation of lamellar phase. Examples of suitable liquid fatty acids include oleic acid, isostearic acid, linoleic acid, linolenic acid, ricinoleic acid, elaidic acid, arichidonic acid, myristoleic acid, palmitoleic acid, and mixtures thereof. Examples of suitable ester derivatives include propylene glycol isostearate, propylene glycol oleate, glyceryl isostearate, glyceryl oleate, polyglyceryl diisostearate and mixtures thereof. Examples of alcohols include oleyl alcohol and isostearyl alcohol. Examples of ether derivatives include isosteareth or oleth carboxylic acid; or isosteareth or oleth alcohol. The structuring agent may be defined as having melting point below about 25° C.

The composition can comprise both an anisotropic and/or an isotropic phase. In a particular embodiment, the structured surfactant is in a visibly distinct phase of the composition.

If present, the composition may comprise a rheology modifier, wherein said rheology modifier comprises cellulosic rheology modifiers, cross-linked acrylates, cross-linked maleic anhydride co-methylvinylethers, hydrophobically modified associative polymers, or a mixture thereof.

An electrolyte, if used, can be added per se to the multiphase composition or it can be formed in situ via the counterions included in one of the raw materials. The electrolyte may include an anion comprising phosphate, chloride, sulfate or citrate and a cation comprising sodium, ammonium, potassium, magnesium or mixtures thereof. The electrolyte may be sodium chloride, ammonium chloride, sodium or ammonium sulfate. The electrolyte may be added to the structured surfactant phase of the multiphase composition in the amount of from about 0.1 wt % to about 15 wt % by weight, alternatively from about 1 wt % to about 6 wt % by weight, and alternatively from about 3 wt % to about 6 wt %, by weight of the structured surfactant composition.

In one embodiment of the present invention, the personal care composition comprises a structured surfactant phase comprising a mixture of at least one nonionic surfactant, and an electrolyte. In another embodiment, the surfactant phase can comprise a mixture of surfactants, water, at least one anionic surfactant, an electrolyte, and at least one alkanolamide.

Aqueous Carrier

The shampoo compositions of the present invention comprise an aqueous carrier. Typically, the compositions of the present invention are in the form of pourable liquids (under ambient conditions). The compositions, therefore, comprise an aqueous carrier at a level of at least about, alternatively from about 20% to about 95%, and alternatively from about 60% to about 85%, by weight of the compositions. The aqueous carrier may comprise water, or a miscible mixture of water and organic solvent. The aqueous carrier may also comprise water with minimal or no significant concentrations of organic solvent, except as otherwise incidentally incorporated into the composition as minor ingredients of other components.

Additional Components

The compositions of the present invention may further comprise one or more optional components known for use in hair care or personal care products, provided that the optional components are physically and chemically compatible with the components described herein, or do not otherwise unduly impair product stability, aesthetics or performance. Individual concentrations of such optional components may range from about 0.001% to about 10% by weight of the compositions.

Non-limiting examples of optional components for use in the composition include cationic polymers, conditioning agents (hydrocarbon oils, fatty esters, silicones), anti-dandruff agents, suspending agents, viscosity modifiers, dyes, nonvolatile solvents or diluents (water soluble and insoluble), pearlescent aids, foam boosters, additional surfactants or nonionic co-surfactants, pediculocides, pH adjusting agents, perfumes, preservatives, chelants, proteins, skin active agents, sunscreens, UV absorbers, and vitamins.

A. Dispersed Particles

The composition of the present invention may include dispersed particles. Particles useful in the present invention can be inorganic, synthetic, or semi-synthetic in origin. If present in the compositions of the present invention, dispersed particles are incorporated in an amount from about 0.025% to about 20%, alternatively from about 0.05% to about 10%, alternatively from about 0.1% to about 5%, alternatively from about 0.25% to about 3%, and alternatively from about 0.5% to about 2%, by weight of the composition.

B. Nonionic Polymers

Polyalkylene glycols having a molecular weight of more than about 1000 are useful herein. Useful are those having the following general formula:

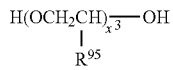

wherein $R^{95}$ is selected from the group consisting of H, methyl, and mixtures thereof. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

C. Additional Conditioning Agents

The compositions of the present invention may also comprise one or more conditioning agents which are in addition to the dispersed gel network phase. Conditioning agents include materials which are used to give a particular conditioning benefit to hair and/or skin. The conditioning agents useful in the compositions of the present invention typically comprise a water-insoluble, water-dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

In one embodiment, the shampoo composition of the present invention further comprises a non-volatile silicone oil. For an opaque composition embodiment, the shampoo composition comprises a non-volatile silicone oil having a particle size as measured in the shampoo composition from about 1 μm to about 50 μm. In an embodiment of the present invention for small particle application to the hair, the shampoo composition comprises a non-volatile silicone oil having a particle size as measured in the shampoo composition from about 100 nm to about 1 μm. For a substantially clear composition embodiment, the shampoo composition comprises a non-volatile silicone oil having a particle size as measured in the shampoo composition of less than about 100 nm.

When present, the one or more conditioning agents are in an amount from about 0.01% to about 10%, alternatively from about 0.1% to about 8%, and alternatively from about 0.2% to about 4%, by weight of the composition.

The conditioning agents may be present in the dispersed gel network phase or may be added to the final shampoo composition as a separate component such that they are present primarily in the continuous phase of the shampoo.

D. Anti-Dandruff Actives

The compositions of the present invention may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the components of the composition, and should not otherwise unduly impair product stability, aesthetics or performance.

When present in the composition, the anti-dandruff active is included in an amount from about 0.01% to about 5%, alternatively from about 0.1% to about 3%, and alternatively from about 0.3% to about 2%, by weight of the composition.

E. Humectants

The compositions of the present invention may contain a humectant. The humectants herein are selected from the group consisting of polyhydric alcohols, water soluble alkoxylated nonionic polymers, and mixtures thereof. The humectants, when used herein, may be present in an amount by weight of the composition from about 0.1% to about 20%, alternatively from about 0.5% to about 5%.

F. Structurants and Suspending Agent

The compositions of the present invention may further comprise a structurant or suspending agent at concentrations effective for suspending water-insoluble material in dispersed form in the compositions or for modifying the viscosity of the composition. Such concentrations range from about 0.02% to about 10%, alternatively from about 0.02% to about 5.0%, alternatively from about 0.02% to about 1.5% by weight of the composition.

Suspending agents useful herein include crystalline suspending agents which can be categorized as acyl derivatives, long chain amine oxides, and mixtures thereof. These suspending agents are described in U.S. Pat. No. 4,741,855. These suspending agents may include ethylene glycol esters of fatty acids having from about 16 to about 22 carbon atoms. Alternatives include ethylene glycol stearates, both mono and distearate, and the distearate containing less than about 7% of the mono stearate.

The use of hydrogenated castor oil structurant (such as commercial name: Thixcin R, supplied by Elementis Specialties) can assist with the formulation using higher levels of fatty alcohol in the gel network. The use of hydrogenated castor oil results in improved formulation flexibility by producing (i) a dispersion having high concentration of the structurant (more efficient use of the plant vessels), and (ii) a crystal habit/form that results in a higher yield stress in the final product, imparting high stability, for a given amount structurant. In addition, as a result of needing less of the more effective structurant, less structurant residue is observed on hair after the use of the personal care product.

To achieve a shampoo composition comprising less structurant, while also delivering conditioning and shine to the hair of the consumers in use, a premix composition comprising hydrogenated castor oil is formed by combining, under high shear, from about 0.30% to about 4% by weight of the premix composition of hydrogenated castor oil ("HCO") structurant, from about 15% to about 40% by weight of the premix composition of surfactant, and from about 60% to about 80 by weight of the premix composition of an aqueous solution such as water together and heating to from about 65° C. to about 84° C. and pH adjusting to from about 5 to about 12, alternatively from about 6 to about 8. The hydrogenated castor oil premix composition is then mixed for about 5-20 minutes. The hydrogenated castor oil premix composition is then cooled from about 60° C. to about 20° C. under low shear at a rate of from about 10 to about 1° C. per minute. The resulting hydrogenated castor oil premix composition forms crystals from the HCO. These crystals are fiber like in structure.

G. Other Optional Components

The compositions of the present invention may contain other optional components. Optional components may be present in the dispersed gel network phase or may be added to the final shampoo composition as separate components.

For example, the compositions of the present invention may contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts. The compositions of present invention may further comprise materials useful for hair loss prevention and hair growth stimulants or agents.

Any other suitable optional component can also be included in the composition of the present invention, such as those ingredients that are conventionally used in given product types. The CTFA Cosmetic Ingredient Handbook, Tenth Edition (2004), published by the Cosmetic, Toiletry, and Fragrance Association, Inc., Washington, D.C., describes a wide variety of nonlimiting materials that can be added to the composition herein. Examples of these ingredient classes include, but are not limited to: abrasives, absorbents, aesthetic components such as perfumes and fragrances, pigments, colorings/colorants, essential oils, skin sensates, astringents, etc. (e.g., clove oil, menthol, camphor, *eucalyptus* oil, eugenol, menthyl lactate, witch hazel distillate), anti-acne agents, anti-caking agents, anti-foaming agents, antimicrobial agents (e.g., iodopropyl butylcarbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g., hydroquinone, kojic acid, ascorbic acid, magnesium ascorbyl phosphate, ascorbyl glucoside, pyridoxine), enzymes, coenzymes, skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), thickeners (including a mono- or divalent salt such as sodium chloride), and vitamins, their derivatives, and combinations thereof.

When certain oil-soluble components, such as perfumes and fragrances, amino acids, water-insoluble vitamins, and the like, are present in the dispersed gel network phase, either by incorporating such components directly into the gel network component pre-mix or separately into the shampoo composition and consequently some amount of such components migrate into the dispersed gel network phase during equilibration, they may be effectively deposited on hair and/or skin. To obtain very effective deposition of oil-soluble components on hair and/or skin via their presence in the dispersed gel network phase, oil-soluble component compositions which comprise no less than about 60% of ingredients having a Clog P of about 3 or higher may be used. For further discussion on Clog P and how to determine its value for a variety of materials, see, for example, U.S. Pat. Nos. 5,849,310 and 5,500,154 as well as EP 1 533 364.

Zero Shear Viscosity

The shampoo composition can have a zero shear viscosity above 30,000 cps; alternatively, from about 60,000 cps to about 90,000 cps; alternatively, from about 90,000 cps to about 300,000 cps; alternatively, In a third embodiment, from about 150,000 cps to about 300,000 cps; and alternatively greater than 300,000 cps. [1,000 cps=1 Pa·s]

It is believed that by elevating the zero shear viscosity of the product, increased product mounding in-hand may be achieved, giving a richer, more luxurious product appearance and therein connote higher product conditioning. Additionally, it is believed that a higher product zero shear viscosity can also increase product phase stability on shelf.

The zero shear viscosity of shampoo may be obtained by using the Discovery Hybrid Rheometer (DHR-3) that is manufactured by TA Instruments, headquartered in New Castle, Del. The geometry and procedure used herein to generate the zero shear product viscosity data are as follows:

Geometry: 40 mm 1.995o cone (with a Peltier steel plate)
Procedure:
Step 1) Conditioning-Sample:
Temperature 25° C. Inherit Set Point: Off
Soak Time 10.0 s Wait For Temperature: On
Wait for axial force: Off Perform preshear: Off Perform equilibration: On Duration 60.0 s
Step 2) Flow-Sweep:
Temperature 25° C. Inherit Set Point: Off
Soak Time 0.0 s Wait For Temperature: Off
Logarithmic sweep
Stress 1 to 300 Pa
Points per decade 10
Steady state sensing: Off Equilibration time 10.0 s
Averaging time 5.0 s
Scaled time average: Off
Step 3) Conditioning-End Of Test:
Set temperature: On Temperature 25° C.
Set temperature system idle (only if axial force control is active): Off

| | Zero Shear Viscosity | | | | | |
|---|---|---|---|---|---|---|
| Product | In-Market Conditioner Chassis [a] | In-Market Shampoo Chassis [b] | Comparative Example A | Shampoo Example 5 | Shampoo Example 8 | Shampoo Example 11 |
| Zero Shear Viscosity (Pa · s) | 19,887 | 55 | 88 | 165 | 197 | 289 |

[a] Pantene Extra Damage Care Conditioner,
[b] Pantene Expert Color Shampoo

Zero shear viscosity values were calculated using the Carreau viscosity equation, which is derived from the Carreau model (1972). The Carreau model is used to describe the shear thinning behavior of a product over wide ranges of shear rates, specifically in instances where limitations in the predictions of other models (e.g. Power-Law) at the ends of said ranges exist.

$$\frac{\mu - \mu_\infty}{\mu_0 - \mu_\infty} = [1 + (\lambda \dot{\gamma}_{yx})^2]^{(n-1)/2}$$

Lather Quality

The present invention also includes shampoo compositions which exhibit a shampoo-like lather profile (when at elevated gel network levels), as is characterized herein by the Krüss Dynamic Foam Analyzer (DFA100). Lather of good quality is characterized herein by a relatively high bubble count half life and final bubble count, while maintaining a relatively small bubble size. These parameters are believed to describe both lather stability and creaminess.

| | Kruss DFA100 Lather Data | | | | | |
|---|---|---|---|---|---|---|
| Product | In-Market Conditioner Chassis [a] | In-Market Shampoo Chassis [b] | Comparative Example A | Shampoo Example 5 | Shampoo Example 8 | Shampoo Example 11 |
| Bubble Count Half Life Time (seconds) | 87 | 132 | 115 | 138 | 175 | 123 |
| Final Bubble Count per $mm^2$ | 23 | 82 | 56 | 101 | 113 | 61 |
| Final Mean Bubble Area ($\mu m^2$) | 45,686 | 12,470 | 18,898 | 9,906 | 9,393 | 16,499 |

[a] Pantene Extra Damage Care Conditioner,
[b] Pantene Expert Color Shampoo

Conditioning Test

Another aspect of the present invention includes the benefit of wet hair conditioning, which was determined qualitatively through the use of a test panel. Said panel was comprised of about 5-10 consumers/panelists who were asked to rate treated hair tresses for ease of wet combing using a 7 pt scale (7=very easy to comb, 1=very difficult to comb).

Procedure for Preparing Treated Hair Tresses

Hair tresses are hung over a sink and pre-wetted with water for about 30 seconds. The tresses are then sandwiched between one's index and middle fingers and pulled through the fingers to remove excess water. 0.1 cc of shampoo composition per gram of hair is applied to each hair tress (front and back), in a zig-zag manner down the length of each tress. The shampoo is brushed into each hair tress, for about 30 seconds, using a small, Goody®, stiff-bristle, plastic brush. Each hair tress is then rinsed with water for about 30 seconds. The tresses are then sandwiched between one's index and middle fingers and pulled through the fingers to remove excess water. The hair tresses are then dried using a hot box to dry the hair tresses in between each cycle. Water used for pre-wetting and rinsing hair tresses is typically at a temperature of about 100° F. and a pressure of about 1.5 gal/min. The water is typically at a hardness of about 7 grains/gallon to about 13 grains/gallon.

The above-steps, with the exception of the pre-wetting step, are then repeated a minimum of three times for each hair tress so that all hair tresses have a minimum number of treatment cycles when evaluated by a panelist. The grades were then tallied for each product, the average scores for which may be found in the table below:

| | Wet Combing Results | | | | |
|---|---|---|---|---|---|
| | In-Market Conditioner Chassis [a] | In-Market Shampoo Chassis [b] | Comparative Example A | Shampoo Example 5 | Shampoo Example 11 |
| Avg. Wet Combing Grade | 6.6 [c], 7.0 [d] | 5.8 [c], 5.6 [d] | 4.8 [c] | 5.9 [d] | 5.2 [d] |

[a] Pantene Extra Damage Care Conditioner,
[b] Pantene Expert Color Shampoo
[c] Test #1,
[d] Test #2

The above wet combing test results show an advantage in wet combing for the in-market shampoo chassis, making the hair tress easier to comb, when compared to Comparative Example A, which represents a single variable increase in gel network in comparison. Shampoo Example 5 represents a change made to the cationic deposition polymer system of Comparative Example A, in addition to a reduction in silicone, wherein Shampoo Example 5 provided equal or better (easier) wet combing of the treated hair tress when compared back to the in-market shampoo.

Process of Making a Shampoo Composition

An aspect of the invention relates to a process of making a shampoo composition of the present invention. The process of making a shampoo composition comprises (a) combining a fatty alcohol, a secondary surfactant, and water at a temperature sufficient to allow partitioning of the secondary surfactant and the water into the fatty alcohol to form a pre-mix; (b) cooling the pre-mix below the chain melt temperature of the fatty alcohol to form a gel network; (c) adding the gel network to one or more detersive surfactants and an aqueous carrier to form a shampoo composition which comprises a dispersed gel network phase having a melt transition temperature of at least about 38° C.

As discussed above, in one embodiment of the present invention, the gel network component is prepared as a separate pre-mix, which, after being cooled, is subsequently incorporated with the other components of the shampoo composition. More specifically, the gel network component of the present invention may be prepared by heating the fatty alcohol, the secondary surfactant, and water to a level in the range of about 75° C. to about 90° C. and mixing. This mixture is cooled to a level in the range of about 27° C. to about 35° C. by, for example, passing the mixture through a heat exchanger. As a result of this cooling step, at least about fifty percent of the mixture of the fatty alcohol and the secondary surfactant crystallize to form a crystalline gel network.

Alternative methods of preparing the gel network component include sonication and/or milling of the fatty alcohol, the secondary surfactant, and water, while these components are heated, to reduce the particle size of the melted fatty alcohol phase. This results in an increase in surface area of the fatty alcohol phase, which allows the secondary surfactant and the water to swell the fatty alcohol phase. Another suitable variation in preparing the gel network includes heating and mixing the fatty alcohol and the secondary surfactant first, and then adding that mixture to the water.

An alternative process of preparing the shampoo comprising the steps of: combining a fatty alcohol and a surfactant in a weight ratio of fatty alcohol to surfactant of about 1:1 to about 40:1 and at a temperature sufficient to allow partitioning of the surfactant into the fatty alcohol to form a premix; cooling the premix below the chain melt temperature of the fatty alcohol to form a solid crystalline gel network; and adding the solid crystalline gel network to a detersive surfactant and an aqueous carrier to form a shampoo composition.

Method of Use

The compositions of the present invention are used in a conventional manner for cleansing and conditioning hair or skin, including scalp, face, and body. Generally, a method of treating hair or skin of the present invention comprises applying the composition of the present invention to the hair or skin. More specifically, an effective amount of the composition is applied to the hair or skin, which has been wetted with water, and then the composition is rinsed off. Such effective amounts generally range from about 1 g to about 50 g, alternatively from about 1 g to about 20 g. Application to the hair typically includes working the composition through the hair such that most or all of the hair is contacted with the composition.

The method for treating the hair or skin comprises the steps of: (a) wetting the hair or skin with water; (b) applying an effective amount of the shampoo composition to the hair or skin, and (c) rinsing the applied areas of skin or hair with water. These steps can be repeated as many times as desired to achieve the desired cleansing and conditioning benefit.

In one embodiment, the shampoo composition of the present invention advantageously is used to treat damaged hair. Damaged hair may include hair selected from permed hair, oxidatively colored hair, and mechanically damaged hair.

In another embodiment, the shampoo composition is used to treat skin, such as the scalp, the face, and the body.

The shampoo compositions of this invention may be used as liquids, solids, semi-solids, flakes, gels, placed in a pressurized container with a propellant added, or used in a pump spray form. The viscosity of the product may be selected to accommodate the form desired.

NON-LIMITING EXAMPLES

The shampoo compositions illustrated in the following Examples illustrate specific embodiments of the shampoo compositions of the present invention, but are not intended to be limiting thereof. Other modifications can be undertaken by the skilled artisan without departing from the spirit and scope of this invention. These exemplified embodiments of the shampoo composition of the present invention provide enhanced conditioning benefits to the hair.

The shampoo compositions illustrated in the following Examples are prepared by conventional formulation and mixing methods, an example of which is set forth below. All exemplified amounts are listed as weight percents and exclude minor materials such as diluents, preservatives, color solutions, imagery ingredients, botanicals, and so forth, unless otherwise specified. All percentages are based on weight unless otherwise specified.

Preparation of the Gel Network Pre-Mix

To prepare the gel network pre-mix, the water is heated to about 74° C. and the fatty alcohol and secondary surfactant (e.g. Sodium Laureth Sulfate) are added to it. After incorporation, this mixture is passed through a mill and heat exchanger where it is cooled to about 32° C. As a result of this cooling step, the fatty alcohol, the secondary surfactant, and the water form a crystalline gel Network Gel Network Pre-Mix Example Table of Gel Network Premix Example

| Premix | % |
|---|---|
| Sodium Laureth-1 Sulfate | 11.00 |
| Stearyl Alcohol | 7.71 |
| Cetyl Alcohol | 4.29 |
| Water | QS |

Preparation of Final Shampoo Compositions

The following examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions. The levels given reflect the weight percent of the active material, unless otherwise specified. A level of perfume and/or preservatives may also be included in the following examples. Viscosity modifiers may also be included (including but not limited to sodium chloride and sodium xylene sulfonate) to adjust product rheology/viscosity to meet desired consumer targets. pH modifiers may also be used (e.g. Citric Acid) to adjust product pH to meet desired targets.

Shampoo Examples 1-12

|  | Example | | | | | |
|---|---|---|---|---|---|---|
|  | 1 | 2 | 3 | 4 | 5 | 6 |
| Sodium Lauryl Sulfate | 5.92 | 7.12 | 7.57 | 6.83 | 7.57 | 8.48 |
| Sodium Laureth-1 Sulfate | 3.42 | 3.32 | 3.58 | 3.95 | 3.58 | 4.11 |
| Sodium Laureth Sulfate n > 1 | 3.66 | 3.56 | 3.85 | 4.22 | 3.85 | 5.41 |
| Cocamidopropyl betaine | 2.00 | 0.00 | 1.70 | 1.70 | 1.70 | 1.70 |
| Lauryl Hydroxysultain | 1.00 | 0.00 | 0.00 | 0.00 | 0.00 | 0.00 |
| Cocomonoethanolamide | 1.00 | 2.50 | 0.00 | 1.00 | 0.00 | 0.00 |
| Laureth-4 | 0.00 | 1.00 | 0.00 | 0.00 | 0.00 | 0.00 |

-continued

| | | | | | | |
|---|---|---|---|---|---|---|
| Stearyl Alcohol | 3.86 | 2.89 | 2.25 | 2.89 | 2.25 | 1.93 |
| Cetyl Alcohol | 2.14 | 1.61 | 1.25 | 1.61 | 1.25 | 1.07 |
| Dimethicone 330M | 0.00 | 0.00 | 0.00 | 0.50 | 0.00 | 0.00 |
| Dimethicone | 0.00 | 2.00 | 1.00 | 1.00 | 1.00 | 1.50 |
| Guar Hydroxy-propyltrimonium Chloride (3196) | 0.20 | 0.25 | 0.20 | 0.00 | 0.20 | 0.20 |
| Guar Hydroxy-propyltrimonium Chloride (BF17) | 0.30 | 0.00 | 0.10 | 0.50 | 0.40 | 0.30 |
| Polyquaternium-10 | 0.00 | 0.25 | 0.10 | 0.00 | 0.00 | 0.00 |
| Ethylene Glycol Distearate | 0.00 | 1.47 | 0.00 | 0.00 | 0.00 | 0.00 |
| Thixcin R | 0.06 | 0.00 | 0.06 | 0.06 | 0.06 | 1.20 |
| Polyquaternium-76 | 0.10 | 0.00 | 0.10 | 0.00 | 0.00 | 0.00 |
| Polyquaternium-6 | 0.00 | 0.08 | 0.15 | 0.10 | 0.00 | 0.00 |
| EDTA | 0.16 | 0.16 | 0.16 | 0.16 | 0.16 | 0.16 |
| Citric Acid | 0.28 | 0.28 | 0.28 | 0.28 | 0.28 | 0.28 |
| Sodium Benzoate | 0.25 | 0.25 | 0.25 | 0.25 | 0.25 | 0.25 |
| Water | QS | QS | QS | QS | QS | QS |
| Total Anionic | 13 | 14 | 15 | 15 | 15 | 18 |
| Zero Shear Viscosity (Pa·s) | — | — | — | — | 165 | — |

| | Example | | | | | |
|---|---|---|---|---|---|---|
| | 7 | 8 | 9 | 10 | 11 | 12 |
| Sodium Lauryl Sulfate | 7.57 | 7.57 | 6.21 | 7.57 | 7.57 | 7.57 |
| Sodium Laureth-1 Sulfate | 3.58 | 3.58 | 2.80 | 3.58 | 3.58 | 3.58 |
| Sodium Laureth Sulfate n > 1 | 3.85 | 3.85 | 4.12 | 3.85 | 3.85 | 3.85 |
| Cocamidopropyl betaine | 1.70 | 1.70 | 3.00 | 1.70 | 1.70 | 1.70 |
| Lauryl Hydroxysultain | 0.00 | 0.00 | 0.00 | 0.00 | 0.00 | 0.00 |
| Cocomonoethanolamide | 0.00 | 0.00 | 0.00 | 0.00 | 0.00 | 0.00 |
| Laureth-4 | 0.00 | 0.00 | 0.00 | 0.00 | 0.00 | 0.00 |
| Stearyl Alcohol | 2.25 | 3.09 | 3.86 | 3.09 | 5.14 | 3.21 |
| Cetyl Alcohol | 1.25 | 1.71 | 2.14 | 1.71 | 2.86 | 1.79 |
| Dimethicone 330M | 0.00 | 0.00 | 0.00 | 0.00 | 0.00 | 0.00 |
| Dimethicone | 1.00 | 1.00 | 1.00 | 0.00 | 1.00 | 1.50 |
| Guar Hydroxy-propyltrimonium Chloride (3196) | 0.40 | 0.20 | 0.30 | 0.20 | 0.20 | 0.40 |
| Guar Hydroxy-propyltrimonium Chloride (BF17) | 0.00 | 0.40 | 0.00 | 0.50 | 0.40 | 0.10 |
| Polyquaternium-10 | 0.10 | 0.00 | 0.20 | 0.00 | 0.00 | 0.10 |
| Ethylene Glycol Distearate | 0.00 | 0.00 | 0.00 | 0.00 | 0.00 | 0.00 |
| Thixcin R | 0.06 | 0.06 | 0.06 | 0.06 | 0.06 | 0.06 |
| Polyquaternium-76 | 0.00 | 0.00 | 0.00 | 0.00 | 0.00 | 0.00 |
| Polyquaternium-6 | 0.10 | 0.00 | 0.00 | 0.00 | 0.00 | 0.00 |
| EDTA | 0.16 | 0.16 | 0.16 | 0.16 | 0.16 | 0.16 |
| Citric Acid | 0.28 | 0.28 | 0.28 | 0.28 | 0.28 | 0.28 |
| Sodium Benzoate | 0.25 | 0.25 | 0.25 | 0.25 | 0.25 | 0.25 |
| Water | QS | QS | QS | QS | QS | QS |
| Total Anionic | 15 | 15 | 12 | 15 | 15 | 15 |
| Zero Shear Viscosity (Pa·s) | — | 197 | — | — | 289 | — |

| Comparative Example | A |
|---|---|
| Sodium Lauryl Sulfate | 7.57 |
| Sodium Laureth-1 Sulfate | 3.58 |
| Sodium Laureth Sulfate n > 1 | 3.85 |
| Cocamidopropyl betaine | 1.70 |
| Lauryl Hydroxysultain | 0.00 |
| Cocomonoethanolamide | 0.00 |
| Laureth-4 | 0.00 |
| Stearyl Alcohol | 2.25 |
| Cetyl Alcohol | 1.25 |
| Dimethicone 330M | 0.00 |
| Dimethicone | 2.00 |
| Guar Hydroxypropyltrimonium Chloride (3196) | 0.30 |
| Guar Hydroxypropyltrimonium Chloride (BF17) | 0.00 |
| Polyquaternium-10 | 0.10 |

-continued

| Comparative Example | A |
|---|---|
| Ethylene Glycol Distearate | 0.00 |
| Thixcin R | 0.06 |
| Polyquaternium-76 | 0.00 |
| Polyquaternium-6 | 0.15 |
| EDTA | 0.16 |
| Citric Acid | 0.28 |
| Sodium Benzoate | 0.25 |
| Water | QS |
| Total Anionic | 15 |
| Zero Shear Viscosity (Pa·s) | 88 |

| Ingredient | Supplied As |
|---|---|
| Polyquaternium-76 | Polyquaternium-76 10% active from Rhodia |
| Polyquaternium-6 | Mirapol 100S from Rhodia |
| Jaguar C17 | Jaguar C17 from Rhodia |
| Guar 3196 | N-Hance 3196 from Hercules Aqualon Div |
| Guar BF17 | N-Hance BF17 from ASI |
| C500 | Jaguar C500 from Rhodia |
| Dimethicone 330M | Dimethicone 330M from Momentive |
| Dimethicone | Besil DM5500 |
| Thixcin R | Hydrogenated Castor Oil |

Examples/Combinations

A. A shampoo composition comprising:
  a. a dispersed gel network phase comprising:
    i. from about 2.8 weight % to about 8 wt % of one or more fatty alcohols, by weight of said shampoo composition;
    ii. at least 0.01% of one or more secondary surfactants by weight of said shampoo composition, wherein the secondary surfactant comprises sodium laureth-n sulfate wherein n is from about 0 to about 5; and
    iii. water; and
  b. from about 5% to about 50% of a detersive surfactant, by weight of said shampoo composition;
  c. from about 0.02% to about 1.50% of a material, by weight of said shampoo composition, selected from the group consisting of structurants, suspending agents and mixtures thereof;
  d. from about 0.5 to about 1% of a cationic deposition polymer, by weight of said shampoo composition;
  e. at least 20% of an aqueous carrier, by weight of said shampoo composition.

B. A method of making a shampoo composition comprising:
  f. forming a dispersed gel network phase by combining
    i. from about 2.8 weight % to about 5 wt % of one or more fatty alcohols, by weight of said shampoo composition;
    ii. at least 0.01% of one or more secondary surfactants by weight of said shampoo composition, wherein the secondary surfactant comprises sodium laureth-n sulfate wherein n is from about 0 to about 5; and
    iii. water; and
  g. mixing the dispersed gel network phase into a shampoo base comprising:
    1) from about 5% to about 50% of a detersive surfactant by weight of said shampoo composition;
    2) from about 0.02% to about 1.50% of hydrogenated castor oil by weight of said shampoo composition;
    3) from about 0.5 to about 1% by weight of a cationic deposition polymer;

4) at least 20% of an aqueous carrier, by weight of said shampoo composition.
C. The shampoo composition according to paragraph A-B, wherein said shampoo composition comprises from about 10% to about 17% of said combination of sodium lauryl sulfate and sodium laureth-n sulfate.
D. The shampoo composition according to paragraph A-C, wherein said shampoo composition comprises from about 0.5% to about 2% of a co-surfactant selected from the group consisting of amphoteric, zwitterionic, and non-ionic surfactants, by weight of said shampoo composition.
E. The shampoo composition according to paragraphs A-D, wherein said shampoo composition comprises from about 0.5% to about 1.75% of a co-surfactant selected from the group consisting of amphoteric, zwitterionic, and non-ionic surfactants, by weight of said shampoo composition.
F. The shampoo composition according to paragraphs A-E, wherein said shampoo composition comprises from about 4% to about 9% sodium lauryl sulfate, by weight of said shampoo composition.
G. The shampoo composition according to paragraphs A-F, wherein said shampoo composition comprises from 0.5% to about 5% sodium laureth-1 sulfate, by weight of said shampoo composition.
H. The shampoo composition according to paragraphs A-G wherein said dispersed gel network phase comprises from about 3% to about 14% of one or more fatty alcohols by weight of said shampoo composition.
I. The shampoo composition according to paragraphs A-H, wherein said one or more fatty alcohols is selected from the group consisting of cetyl alcohol, stearyl alcohol, behenyl alcohol, and mixtures thereof.
J. The shampoo composition according to paragraphs A-I, wherein said dispersed gel network phase comprises from about 0.2% to about 15% of one or more secondary surfactants by weight of said shampoo composition.
K. The shampoo composition according to paragraphs A-J, wherein said secondary surfactant is selected from the group consisting of anionic surfactants, cationic surfactants, non-ionic surfactants and mixtures thereof.
L. The shampoo composition according to paragraphs A-K, wherein said secondary surfactant is selected from the group consisting of cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, and mixtures thereof.
M. The shampoo composition according to paragraphs A-L, wherein said secondary surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and mixtures thereof.
N. The shampoo composition according to paragraphs A-M, wherein said dispersed gel network phase further comprises one or more fatty compounds selected from the group consisting of fatty amides, di-fatty ethers, fatty carbamates, fatty acids, fatty esters, fatty phosphorous compounds, fatty sorbitan derivatives, alkyl sulfoxides, and mixtures thereof.
O. The shampoo composition according to paragraphs A-N, wherein said zwitterionic surfactant is a betaine.
P. The shampoo composition according to paragraphs A-O, wherein said zwitterionic surfactant is a sultaine.
Q. The shampoo composition according to paragraphs A-P, wherein said nonionic surfactant is a cocomonethanolamine.
R. The shampoo composition according to paragraphs A-Q, wherein said shampoo composition has a zero shear viscosity that is greater than 30,000 cps
S. The shampoo composition according to paragraphs A-R, wherein said shampoo composition has a zero shear viscosity of from about 35,000 cps to about 15,000,000 cps
T. The shampoo composition according to paragraphs A-S, wherein said shampoo composition does not contain silicone
U. The shampoo composition according to paragraphs A-T, wherein said shampoo composition has a zero shear viscosity that is from about 60,000 cps to about 1,000,000 cps
V. The shampoo composition according to paragraphs A-U, wherein said shampoo composition has a zero shear viscosity that is from about 90,000 cps to about 1,000,000 cps
W. The shampoo composition according to paragraphs A-V, wherein said shampoo composition has a zero shear viscosity that is from about 125,000 cps to about 300,000 cps
X. The shampoo composition according to paragraphs A-W, wherein said shampoo composition does not contain silicone
Y. The shampoo composition according to paragraphs A-X, wherein said shampoo composition has:
  h. a zero shear viscosity that is greater than 30,000 cps;
  i. a bubble count half life that is greater than 120 seconds, as measured by the Kruss DFA100; and
  j. a final bubble count per $mm^2$ that is greater than 60.
Z. A process for preparing the shampoo composition according to paragraphs A-Y, said process comprising the steps of:
  k. combining a fatty alcohol and a surfactant in a weight ratio of fatty alcohol to surfactant of about 1:1 to about 40:1 and at a temperature sufficient to allow partitioning of the surfactant into the fatty alcohol to form a premix;
  l. cooling the premix below the chain melt temperature of the fatty alcohol to form a solid crystalline gel network; and
  m. adding the solid crystalline gel network to a detersive surfactant and an aqueous carrier to form a shampoo composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A shampoo composition comprising:
  a. dispersed gel network phase comprising:
    i. from about 3.5 weight % to about 8 wt % of one or more fatty alcohols, by weight of said shampoo composition; wherein the fatty alcohol is selected from cetyl alcohol, stearyl alcohol, or mixtures thereof;
    ii. at least 0.01% of one or more secondary surfactants by weight of said shampoo composition, wherein the secondary surfactant comprises sodium laureth-n sulfate wherein n is from about 0 to about 5; and
    iii. water; and
  b. from about 5% to about 50% of a detersive surfactant, by weight of said shampoo composition;
  c. from about 0.5% to about 2% of a co-surfactant; wherein the co-surfactant is selected from a betaine, a sultaine, a cocomonethanolamine, and mixtures thereof; by weight of said shampoo composition
  d. from about 0.02% to about 1.50% of a material, by weight of said shampoo composition, selected from the group consisting of structurants, suspending agents and mixtures thereof;
  e. from about 0.5 to about 1% of a cationic deposition polymer, by weight of said shampoo composition; wherein the polymer has a about 0.7 meq/g and weight average molecular weight greater than about 1,000,000;
  f. at least 20% of an aqueous carrier, by weight of said shampoo composition;
wherein said shampoo composition has:
  a. a zero shear viscosity that is greater than 30,000 cps;
  b. a bubble count half life that is greater than 120 seconds, as measured by the Kruss DFA100; and
  c. a final bubble count per $mm^2$ that is greater than 60.
2. A method of making a shampoo composition comprising:
  a. forming a dispersed gel network phase by combining
    i. from about 3.5 weight % to about 8 wt % of one or more fatty alcohols, by weight of said shampoo composition; wherein the fatty alcohol is selected from cetyl alcohol, stearyl alcohol, or mixtures thereof;
    ii. at least 0.01% of one or more secondary surfactants by weight of said shampoo composition, wherein the secondary surfactant comprises sodium laureth-n sulfate wherein n is from about 0 to about 5; and
    iii. water; and
  b. mixing the dispersed gel network phase into a shampoo base comprising:
    i. from about 5% to about 50% of a detersive surfactant by weight of said shampoo composition;
    ii from about 0.02% to about 1.50% of hydrogenated castor oil by weight of said shampoo composition;
    iii. from about 0.5 to about 1% by weight of a cationic deposition polymer; wherein the polymer has a about 0.7 meq/g and weight average molecular weight greater than about 1,000,000;
    iv. from about 0.5% to about 2% of a co-surfactant; wherein the co-surfactant is selected from a betaine, a sultaine, a cocomonethanolamine, and mixtures thereof;
    v. at least 20% of an aqueous carrier, by weight of said shampoo composition
forming a shampoo composition wherein said shampoo composition has:
  a. a zero shear viscosity of from about 35,000 cps to about 15,000,000 cps;
  b. a bubble count half life that is greater than 120 seconds, as measured by the Kruss DFA100; and
  c. a final bubble count per $mm^2$ that is greater than 60.
3. The shampoo composition according to claim 1, wherein said shampoo composition comprises from about 10% to about 17% of said combination of sodium lauryl sulfate and sodium laureth-n sulfate.
4. The shampoo composition according to claim 1, wherein said shampoo composition comprises from about 4% to about 9% sodium lauryl sulfate, by weight of said shampoo composition.
5. The shampoo composition according to claim 1, wherein said shampoo composition comprises from 0.5% to about 5% sodium laureth-1 sulfate, by weight of said shampoo composition.
6. The shampoo composition according to claim 1, wherein said dispersed gel network phase comprises from about 0.2% to about 15% of one or more secondary surfactants by weight of said shampoo composition.
7. The shampoo composition according to claim 1, wherein said secondary surfactant further comprises a surfactant selected from the group consisting of anionic surfactants, cationic surfactants, non-ionic surfactants and mixtures thereof.
8. The shampoo composition according to claim 1, wherein said secondary surfactant further comprises a surfactant selected from the group consisting of cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, and mixtures thereof.
9. The shampoo composition according to claim 1, wherein said secondary surfactant further comprises a surfactant selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate, and mixtures thereof.

10. The shampoo composition according to claim 1, wherein said dispersed gel network phase further comprises one or more fatty compounds selected from the group consisting of fatty amides, di-fatty ethers, fatty carbamates, fatty acids, fatty esters, fatty phosphorous compounds, fatty sorbitan derivatives, alkyl sulfoxides, and mixtures thereof.

11. The shampoo composition according to claim 1, wherein said shampoo composition does not contain silicone.

12. The shampoo composition according to claim 1, wherein said shampoo composition has a zero shear viscosity that is from about 60,000 cps to about 1,000,000 cps.

* * * * *